United States Patent
Pelrine et al.

(10) Patent No.: US 7,911,115 B2
(45) Date of Patent: *Mar. 22, 2011

(54) MONOLITHIC ELECTROACTIVE POLYMERS

(75) Inventors: Ronald E. Pelrine, Longmont, CO (US); Roy D. Kornbluh, Palo Alto, CA (US); Qibing Pei, Temecula, CA (US); Joseph S. Eckerle, Redwood City, CA (US)

(73) Assignee: SRI International, Menlo Park, CA (US)

( * ) Notice: Subject to any disclaimer, the term of this patent is extended or adjusted under 35 U.S.C. 154(b) by 793 days.

This patent is subject to a terminal disclaimer.

(21) Appl. No.: 11/777,036

(22) Filed: Jul. 12, 2007

(65) Prior Publication Data
US 2010/0026143 A1    Feb. 4, 2010

Related U.S. Application Data

(60) Continuation of application No. 11/375,930, filed on Mar. 14, 2006, now Pat. No. 7,362,032, which is a division of application No. 10/393,506, filed on Mar. 18, 2003, now Pat. No. 7,064,472, which is a continuation-in-part of application No. 09/619,847, filed on Jul. 20, 2000, now Pat. No. 6,812,624, and a continuation-in-part of application No. 09/779,203, filed on Feb. 7, 2001, now Pat. No. 6,664,718.

(60) Provisional application No. 60/144,556, filed on Jul. 20, 1999, provisional application No. 60/153,329, filed on Sep. 10, 1999, provisional application No. 60/161,325, filed on Oct. 25, 1999, provisional application No. 60/181,404, filed on Feb. 9, 2000, provisional application No. 60/187,809, filed on Mar. 8, 2000, provisional application No. 60/192,237, filed on Mar. 27, 2000, provisional application No. 60/184,217, filed on Feb. 23, 2000, provisional application No. 60/181,404, filed on Feb. 9, 2000.

(51) Int. Cl.
*H02N 2/00* (2006.01)

(52) U.S. Cl. ......... 310/328; 310/330; 310/366; 310/800

(58) Field of Classification Search .................. 310/317, 310/328, 330, 366, 800
See application file for complete search history.

(56) References Cited

U.S. PATENT DOCUMENTS 3,403,234 A    9/1968    Barnes, Jr.
(Continued)

FOREIGN PATENT DOCUMENTS

JP    4-353279    12/1992
(Continued)

OTHER PUBLICATIONS

Ajluni, Cheryl, "Pressure Sensors Strive to Stay on Top, New Silicon Micromachining Techniques and Designs Promise Higher Performance", *Electronic Design—Advanced Technology Series*, Oct. 3, 1994, pp. 67-74.

(Continued)

*Primary Examiner* — Thomas M Dougherty
(74) *Attorney, Agent, or Firm* — John E. Mrozinski, Jr.; Noland J. Cheung

(57) ABSTRACT

The present invention relates to polymers, transducers and devices that convert between electrical and mechanical energy. When a voltage is applied to electrodes contacting an electroactive polymer, the polymer deflects. This deflection may be used to do mechanical work. Similarly, when the electroactive polymer deflects, an electric field is produced in the polymer. This electric field may be used to produce electrical energy. An active area is a portion of a polymer having sufficient electrostatic force to enable deflection of the portion and/or sufficient deflection to enable a change in electrostatic force. The present invention relates to transducers and devices including multiple active areas. The invention also relates to methods for actuating one or more active areas.

20 Claims, 8 Drawing Sheets

U.S. PATENT DOCUMENTS

| | | |
|---|---|---|
| 3,832,580 A | 8/1974 | Yamamuro et al. |
| 4,290,983 A | 9/1981 | Sasaki et al. |
| 4,342,936 A | 8/1982 | Marcus et al. |
| 4,384,394 A | 5/1983 | Lemonon et al. |
| 4,400,634 A | 8/1983 | Micheron |
| 4,401,911 A | 8/1983 | Ravinet et al. |
| 4,518,555 A | 5/1985 | Ravinet et al. |
| 4,783,888 A | 11/1988 | Fujii et al. |
| 4,843,275 A | 6/1989 | Radice |
| 4,879,698 A | 11/1989 | Langberg |
| 4,885,783 A | 12/1989 | Whitehead et al. |
| 4,969,197 A | 11/1990 | Takaya |
| 5,024,872 A | 6/1991 | Wilson et al. |
| 5,229,979 A | 7/1993 | Scheinbeim et al. |
| 5,240,004 A | 8/1993 | Walinski et al. |
| 5,250,784 A | 10/1993 | Muller et al. |
| 5,254,296 A | 10/1993 | Perlman |
| 5,356,500 A | 10/1994 | Scheinbeim et al. |
| 5,369,995 A | 12/1994 | Scheinbeim et al. |
| 5,430,565 A | 7/1995 | Yamanouchi et al. |
| 5,438,553 A | 8/1995 | Wilson et al. |
| 5,440,194 A | 8/1995 | Beurrier |
| 5,495,137 A | 2/1996 | Park et al. |
| 5,589,725 A | 12/1996 | Haertling |
| 5,642,015 A | 6/1997 | Whitehead et al. |
| 5,751,090 A | 5/1998 | Henderson |
| 5,835,453 A | 11/1998 | Wynne et al. |
| 5,902,836 A | 5/1999 | Bennett et al. |
| 5,915,377 A | 6/1999 | Coffee |
| 5,928,547 A | 7/1999 | Shea et al. |
| 5,977,685 A | 11/1999 | Kurita et al. |
| 6,048,622 A | 4/2000 | Hagood, IV et al. |
| 6,060,811 A | 5/2000 | Fox et al. |
| 6,084,321 A | 7/2000 | Hunter et al. |
| 6,184,608 B1 | 2/2001 | Cabuz et al. |
| 6,184,609 B1 | 2/2001 | Johansson et al. |
| 6,228,533 B1 | 5/2001 | Ohashi |
| 6,248,262 B1 | 6/2001 | Kubotera |
| 6,249,076 B1 | 6/2001 | Madden et al. |
| 6,291,155 B1 | 9/2001 | Raguse |
| 6,376,971 B1 | 4/2002 | Kornbluh et al. |
| 6,379,393 B1 | 4/2002 | Mavroidis et al. |
| 6,379,809 B1 | 4/2002 | Simpson et al. |
| 6,433,689 B1 | 8/2002 | Hovind et al. |
| 6,495,945 B2 | 12/2002 | Yamaguchi et al. |
| 6,514,237 B1 | 2/2003 | Maseda |
| 6,543,110 B1 | 4/2003 | Joseph et al. |
| 6,545,384 B1 | 4/2003 | Kronbluh et al. |
| 6,583,533 B2 | 6/2003 | Kornbluh et al. |
| 6,652,938 B1 | 11/2003 | Nishikawa et al. |
| 6,664,718 B2 | 12/2003 | Pelrine et al. |
| 6,673,533 B1 | 1/2004 | Wohlstadter |
| 6,743,273 B2 | 6/2004 | Chung |
| 6,781,284 B1 | 8/2004 | Pelrine et al. |
| 6,800,155 B2 | 10/2004 | Senecal |
| 6,812,624 B1 | 11/2004 | Pei et al. |
| 6,824,689 B2 | 11/2004 | Wang |
| 6,847,153 B1 | 1/2005 | Balizer |
| 6,911,764 B2 | 6/2005 | Pelrine |
| 6,940,211 B2 | 9/2005 | Pelrine et al. |
| 7,011,760 B2 | 3/2006 | Wang |
| 7,029,056 B2 | 4/2006 | Browne |
| 7,034,432 B1 | 4/2006 | Pelrine |
| 7,049,732 B2 | 5/2006 | Pei |
| 7,063,377 B2 | 6/2006 | Brei |
| 7,075,162 B2 | 7/2006 | Unger |
| 7,104,146 B2 | 9/2006 | Benslimane |
| 7,109,643 B2 | 9/2006 | Hirai |
| 7,144,616 B1 | 12/2006 | Unger |
| 2002/0013545 A1 | 1/2002 | Soltanpour et al. |
| 2002/0050454 A1 | 5/2002 | Shahinpoor |
| 2004/0263028 A1 | 12/2004 | Pei et al. |
| 2005/0085693 A1 | 4/2005 | Belson |
| 2005/0200984 A1 | 9/2005 | Browne |
| 2005/0230546 A1 | 10/2005 | McKnight |
| 2005/0234139 A1 | 10/2005 | Browne |
| 2005/0275246 A1 | 12/2005 | Browne |
| 2006/0057377 A1 | 3/2006 | Harrison |
| 2006/0113878 A1 | 6/2006 | Pei |
| 2006/0118895 A1 | 6/2006 | Unger |
| 2006/0258912 A1 | 11/2006 | Belson |

FOREIGN PATENT DOCUMENTS

| | | |
|---|---|---|
| JP | 5-202707 | 8/1993 |
| JP | 7-240544 | 9/1995 |
| JP | 2005-762463 | 10/1995 |
| JP | 10-321482 | 12/1998 |
| JP | 2001-286162 | 10/2001 |
| WO | WO 87/07218 | 12/1987 |
| WO | WO 89/02658 | 3/1989 |
| WO | WO 95/08905 | 3/1995 |
| WO | WO 98/35529 | 8/1998 |
| WO | WO 99/17929 | 4/1999 |
| WO | WO 99/37921 | 7/1999 |
| WO | WO 01/06575 | 1/2001 |
| WO | WO 01/06579 | 1/2001 |
| WO | WO 01/59852 | 8/2001 |
| WO | WO 2006/121818 | 11/2006 |
| WO | WO 2006/123317 | 11/2006 |
| WO | WO 2007/029275 | 3/2007 |

OTHER PUBLICATIONS

Anderson, R. A., "Mechanical Stress in a Dielectric Solid From a Uniform Electric Field", *The American Physical Society*, 1986, pp. 1302-1307.

Aramaki, S., S. Kaneko, K. Arai, Y. Takahashi, H. Adachi, and K. Yanagisawa. 1995. "Tube Type Micro Manipulator Using Shape Memory Alloy (SMA)," *Proceedings of the IEEE Sixth International Symposium on Micro Machine and Human Science*, Nagoya, Japan, pp. 115-120.

Ashley, S., "Smart Skis and Other Adaptive Structures", *Mechanical Engineering*, Nov. 1995, pp. 77-81.

Bar-Cohen, Yoseph, JPL, *WorldWide Electroactive Polymer Actuators Webhub* webpages 1-7, http://ndeaa.jpl.nasa.gov/nasa-nde/lommas/eap/EAP-web.htm, downloaded Jul. 23, 2001.

Bar-Cohen, Yoseph, JPL, *WorldWide ElectroActive Polymers, EAP (Artificial Muscles) Newsletter*, vol. 1, No. 1, Jun. 1999.

Bar-Cohen, Yoseph, JPL, *WorldWide ElectroActive Polymers, EAP (Artificial Muscles) Newsletter*, vol. 1, No. 2, Dec. 1999.

Bar-Cohen, Yoseph, JPL, WorldWide ElectroActive Polymers, EAP *(Artificial Muscles) Newsletter*, vol. 2, No. 1, Jul. 2000.

Bar-Cohen, Yoseph, JPL, *WorldWide ElectroActive Polymers, EAP (Artificial Muscles) Newsletter*, vol. 2, No. 2, Dec. 2000.

Bar-Cohen, Yoseph, JPL, *WorldWide ElectroActive Polymers, EAP (Artificial Muscles) Newsletter*, vol. 3, No. 1, Jun. 2001.

Baughman, R., L. Shacklette, R. Elsenbaumer, E. Plichta, and C. Becht "Conducting Polymer Electromechanical Actuators," *Conjugated Polymeric Materials: Opportunities in Electronics, Optoelectronics and Molecular Electronics*, eds. J.L. Bredas and R.R. Chance, Kluwer Academic Publishers, The Netherlands, pp. 559-582, 1990.

Baughman, R.H., L.W. Shacklette, and R.L. Elsenbaumer, E.J. Plichta, and C. Becht, "Micro electromechanical actuators based on conducting polymers", in *Molecular Electronics, Materials and Methods*, P.I. Lazarev (ed.), Kluwer Academic Publishers, pp. 267-289 (1991).

Bharti, V., H. S. Xu, G. Shanthi, and Q. M. Zhang, "Polarization and Structural Properties of High Energy Electron Irradiated Poly(vinylidene fluoride-trifluoroethylene) Copolymer Films," to be published in J. Appl. Phys. (2000).

Bharti, V., X.-Z. Zhao, Q. M. Zhang, T. Romotowski, F. Tito, and R. Ting, "Ultrahigh Field Induced Strain and Polarization Response in Electron Irradiated Poly(Vinylidene Fluoride-Trifluoroethylene) Copolymer," *Mat. Res. Innovat.* vol. 2, 57-63 (1998).

Bharti, V., Y. Ye, T.-B. Xu and Q. M. Zhang, "Correlation Between Large Electrostrictive Strain and Relaxor Behavior with Structural Changes Induced in P(VDF-TrFE) Copolymer by electron Irradiation," Mat. Res. Soc. Symp. Proc. vol. 541, pp. 653-659 (1999).

Bharti, V., Z.-Y. Cheng, S. Gross, T.-B. Xu, and Q. M. Zhang, "High electrostrictive strain under high mechanical stress in electron-irradiated poly(vinylidene fluoride-trifluoroethylene) copolymer," *Appl. Phys. Lett*. vol. 75, 2653-2655 (Oct. 25, 1999).

Bobbio, S., M Kellam, B. Dudley, S. Goodwin Johansson, S. Jones, J. Jacobson, F. Tranjan, and T. DuBois, "Integrated Force Arrays," in Proc. IEEE Micro ElectroMechanical Systems Workshop, Fort Lauderdale, Florida Feb. 1993.

Bohon, K., and S. Krause, "An Electrorheological Fluid and Siloxane Gel Based Electromechanical Actuator: Working Toward an Artificial Muscle," to be published in *J. Polymer Sci., Part B. Polymer Phys.* (2000).

Brock, D. L., "Review of Artificial Muscle based on Contractile Polymers," MIT Artificial Intelligence Laboratory, A.I. Memo No. 1330, Nov. 1991.

Caldwell, D., G. Medrano-Cerda, and M. Goodwin, "Characteristics and Adaptive Control of Pneumatic Muscle Actuators for a Robotic Elbow," Proc. IEEE Int. Conference on Robotics and Automation, San Diego, California (May 8-13, 1994).

Calvert, P. and Z. Liu, "Electrically stimulated bilayer hydrogels as muscles," Proceedings of the SPIE International Symposium on Smart Structures and Materials: Electro-Active Polymer Actuators and Devices, Mar. 1-2, 1999, Newport Beach, California, USA, pp. 236-241.

Cheng, Z.-Y., H. S. Xu, J. Su, Q. M. Zhjang, P.-C. Wang, and A. G. MacDiarmid, "High performance of all-polymer electrostrictive systems," Proceedings of the SPIE International Symposium on Smart Structures and Materials: Electro-Active Polymer Actuators and Devices, Mar. 1-2, 1999, Newport Beach, California, USA., pp. 140-148.

Cheng, Z.-Y., T.-B. Xu, V. Bharti, S. Wang, and Q. M. Zhang, "Transverse Strain Responses In the Electrostrictive Poly(Vinylidene Fluoride-Trifluorethylene) Copolymer," *Appl. Phys. Lett.* vol. 74, No. 13, pp. 1901-1903, Mar. 29, 1999.

Chiarelli, P., A. Della Santa, D. DeRossi, and A. Mazzoldi. 1995. "Actuation Properties of Electrochemically Driven Polypyrrole Freestanding Films," *Journal of Intelligent Material Systems and Structures*, vol. 6, pp. 32-37, Jan. 1995.

De Rossi, D., and P. Chiarelli. 1994. "Biomimetic Macromolecular Actuators," *Macro-Ion Characterization, American Chemical Society Symposium Series*, vol. 548, Ch. 40, pp. 517-530.

Dowling, K., *Beyond Faraday-Non Traditional Actuation*, available on the World Wide Web at http://www.frc.ri.cmu.edu/~nivek/OTH/beyond-faraday/beyondfaraday.html, 9 pages. 1994.

Egawa, S. and T. Higuchi, "Multi-Layered Electrostatic Film Actuator," Proc. IEEE Micro Electra Mechanical Systems, Napa Valley, California, pp. 166-171 (Feb. 11-14, 1990).

Elhami, K., and B. Gauthier-Manuel, "Electrostriction of the Copolymer of Vinylidene-Fluoride and Trifluoroethylene," *J. Appl. Phys.* vol. 77 (8), 3987-3990, Apr. 15, 1995.

Flynn, Anita M., L.S. Tavrow, S.F. Bart, R.A. Brooks, D.J. Ehrlich, K.R. Udayakumar, and L.E. Cross. 1992. "Piezoelectric Micromotors for Microrobots," *IEEE Journal of Microelectromechanical Systems*, vol. 1, No. 1, pp. 44-51 (Mar. 1992); also published as *MIT AI Laboratory Memo 1269*, Massachusetts Institute of Technology (Feb. 1991).

Full, R. J. and K. Meijer, "Artificial Muscles Versus Natural Actuators From Frogs to Flies," Proceedings of the 7th SPIE Symposium on Smart Structures and Materials-Electroactive Polymers and Devices (EAPAD) Conference, Mar. 6-8, 2000, Newport Beach, California, USA, pp. 2-9.

Furuhata, T., T. Hirano, and H. Fujita, "Array-Driven Ultrasonic Microactuators," Solid State Sensors and Actuators, 1991, Digest of Tech. Papers, Transducers, pp. 1056-1059.

Furukawa, T., and N. Seo., "Electrostriction as the Origin of Piezoelectricity in Ferroelectric Polymers," *Japanese J. Applied Physics*, vol. 29, No. 4, pp. 675-680 (Apr. 1990).

Gilbertson, R.G., and J.D. Busch. 1994. "Survey of Micro-Actuator Technologies for Future Spacecraft Missions," presented at the conference entitled "Practical Robotic Interstellar Flight: Are We Ready?" New York University and The United Nations, New York. (Aug. 29 and Sep. 1, 1994 ); also published on the World Wide Web at http://nonothinc.com/nanosci/microtech/mems/ten-actuators/gilbertson.html.

Goldberg, Lee, Adaptive-Filtering Developments Extend Noise-Cancellation Applications, *Electronic Design*, Feb. 6, 1995, pp. 34 and 36.

Heydt, R., R. Kornbluh, R. Pelrine, and B. Mason, "Design and Performance of an Electrostrictive Polymer Film Acoustic Actuator", *Journal of Sound and Vibration* (1998)215(2), 297-311.

Heydt, R., R. Pelrine, J. Joseph, J. Eckerle, and R. Kornbluh. "Acoustical Performance of an Electrostrictive Polymer Film Loudspeaker", *Journal of the Acoustical Society of America* vol. 107, pp. 833-839 (Feb. 2000).

Hirano, M., K. Yanagisawa, H. Kuwano, and S. Nakano, "Microvalve with Ultra-low Leakage," Tenth Annual International Workshop on Micro Electromechanical Systems, Nagoya, Japan, *IEEE Proceedings* (Jan. 26-30, 1997), pp. 323-326.

Hirose, S., Biologically Inspired Robots: Snake-like Locomotors and Manipulators, "*Development of the ACM as a Manipulator*", Oxford University Press, New York, 1993, pp. 170-172.

Hunter, I., S. Lafontaine, J. Hollerbach, and P. Hunter, "Fast Reversible NiTi Fibers for Use in MicroRobotics," *Proc. 1991 IEEE Micro Electro Mechanical Systems-MEMS '91*, Nara, Japan, pp. 166-170.

Hunter, I.W., and S. Lafontaine, "A Comparison of Muscle with Artificial Actuators", *Technical Digest of the IEEE Solid-state Sensor and Actuator Workshop*, Hilton Head, South Carolina, Jun. 22-25, 1992, pp. 178-185.

Jacobsen, S., Price, R., Wood, J, Rytting, T., and Rafaelof, M., "A Design Overview of an Eccentric-Motion Electrostatic Microactuator (the Wobble Motor)", *Sensors and Actuators*, 20 (1989) pp. 1-16.

Kaneto, K., M. Kaneko, Y. Min, and A.G. MacDiarmid. 1995. "'Artificial Muscle': Electromechanical Actuators Using Polyaniline Films," *Synthetic Metals 71*, pp. 2211-2212, 1995.

Kawamura, S., K. Minani, and M. Esashi, "Fundamental Research of Distributed Electrostatic Micro Actuator," Technical Digest of the 11th Sensor Symposium, pp. 27-30(1992).

Kondoh Y., and T. Ono. 1991. "Bimorph Type Actuators using Lead Zinc Niobate-based Ceramics," *Japanese Journal of Applied Physics*, vol. 30, No. 9B, pp. 2260-2263, Sep. 1991.

Kornbluh, R. D and R. E. Pelrine., "Dexterous Multiarticulated Manipulator with Electrostrictive Polymer Artificial Muscle," ITAD-7247-QR-96-175, SRI Project No. 7247, Prepared for: Office of Naval Research, Nov. 1996.

Kornbluh, R., G. Andeen, and J. Eckerle, "Artificial Muscle: The Next Generation of Robotic Actuators," presented at the Fourth World Conference on Robotics Research, SME Paper M591-331, Pittsburgh, PA, Sep. 17-19, 1991.

Kornbluh, R., Pelrine, R. Joseph, J., Pei, Q. and Chiba, S., "Ultra-High Strain Response of Elastomeric Polymer Dielectrics", Proc. Materials Res. Soc., Fall meeting, Boston, MA, pp. 1-12, Dec. 1999.

Kornbluh, R., Pelrine, R., Eckerie, J., Joseph, J., "Electrostrictive Polymer Artificial Muscle Actuators", IEEE International Conference on Robotics and Automation, Leuven, Belgium, 1998.

Kornbluh, R., R. Pelrine, J. Joseph, "Elastomeric Dielectric Artificial Muscle Actuators for Small Robots," *Proceedings of the Third IASTED International Conference on Robotics and Manufacturing*, Jun. 14-16, 1995, Cancun, Mexico.

Kornbluh, R., R. Pelrine, Jose Joseph, Richard Heydt, Qibing Pei, Seiki Chiba, 1999. "High-Field Electrostriction Of Elastomeric Polymer Dielectrics For Actuation", Proceedings of the SPIE International Symposium on Smart Structures and Materials: Electro-Active Polymer Actuators and Devices, Mar. 1-2, 1999, Newport Beach, California, USA. pp. 149-161.

Kornbluh, R., R. Pelrine, Q. Pei, S. Oh, and J. Joseph, 2000. "Ultrahigh Strain Response of Field-Actuated Elastomeric Polymers," Proceedings of the 7th SPIE Symposium on Smart Structures and Materials-Electroactive Polymers and Devices (EAPAD) Conference, Mar. 6-8, 2000, Newport Beach, California, USA, pp. 51-64.

Kornbluh, R., R. Pelrine, R. Heydt, and Q. Pei, "Acoustic Actuators Based on the Field-Activated Deformation of Dielectric Elastomers," (2000).

Ktech's PVDF Sensors, http://www.ktech.com/pvdf.htm, Jun. 6, 2001, pp. 1-5.

Lang, J, M. Schlect, and R. Howe, "Electric Micromotors: Electromechanical Characteristics," Proc. IEEE Micro Robots and Teleoperators Workshop, Hyannis, Massachusetts (Nov. 9-11, 1987).

Lawless, W. and R. Arenz, "Miniature Solid-state Gas Compressor," *Rev. Sci Instrum.*, 58(8), pp. 1487-1493, Aug. 1987.

Liu, C., Y. Bar-Cohen, and S. Leary, "Electro-statically stricted polymers (ESSP)," Proceedings of the SPIE International Symposium on Smart Structures and Materials: Electro-Active Polymer Actuators and Devices, Mar. 1-2, 1999, Newport Beach, California, USA., pp. 186-190.

Liu, Y., T. Zeng, Y.X. Wang, H. Yu, and R. Claus, "Self-Assembled Flexible Electrodes on Electroactive Polymer Actuators," Proceedings of the SPIE International Symposium on Smart Structures and Materials: Electro-Active Polymer Actuators and Devices, Mar. 1-2, 1999, Newport Beach, California, USA., pp. 284-288.

M. Greene and J. A. Willett, and Kornbluh, R., "Robotic systems," in ONR Report 32198-2, Ocean Engineering and Marine Systems 1997 Program (Dec. 1997).

Martin, J. and R. Anderson, 1999. "Electrostriction In Field-Structured Composites: Basis For A Fast Artificial Muscle?", *Journal of Chemical Physics*, vol. 111, No. 9, pp. 4273-4280, Sep. 1, 1999.

Measurements Specialties, Inc.—Piezo Home, http://www.msiusa.com/piezo/index.htm, Jun. 6, 2001.

Nguyen, T., Green, M., and Kornbluh, R., "Robotic Systems," in ONR Ocean, Atmosphere, and Space Fiscal Year 1999 Annual Reports (Dec. 1999).

Nguyen, T., J. A. Willett and Kornbluh, R., "Robotic systems," in ONR Ocean, Atmosphere, and Space Fiscal Year 1998 Annual Reports (Dec. 1998).

Ohara, K., M. Hennecke, and J. Fuhrmann, "Electrostriction of polymethylmethacrylates," *Colloid & Polymer Sci.* vol. 280, 164-168 (1982).

Olsson, A., G. Stemme, and E. Stemme, "The First Valve-less Diffuser Gas Pump," Tenth Annual International Workshop on Micro Electromechanical Systems, Nagoya, Japan, *IEEE Proceedings* (Jan. 26-30, 1997), pp. 108-113.

Olsson, A., O. Larsson, J. Holm, L. Lundbladh, O. Ohinan, and G. Stemme. 1997. "Valve-less Diffuser Micropumps Fabricated using Thermoplastic Replication," *Proc. IEEE Micro Electro Mechanical Systems*, Nagoya, Japan, pp. 305-310 (Jan. 26-30, 1997).

Otero, T.F., J. Rodriguez, and C. Santamaria, "Smart Muscle Under Electrochemical Control of Molecular Movement in Polypyrrole Films," *Materials Research Society Symposium Proceedings*, vol. 330, pp. 333-338, 1994.

Otero, T.F., J. Rodriguez, E. Angulo and C. Santamaria, "Artificial Muscles from Bilayer Structures," *Synthetic Metals*, vol. 55-57, pp. 3713-3717 (1993).

Park, S.E., and T. Shrout., "Ultrahigh Strain and Piezoelectric Behavior in Relaxor Based Ferroelectric Single Crystals," *J Applied Physics*, vol. 82, pp. 1804-1811, Aug. 15, 1997.

Pei, Q., O. Inganäs, and I. Lundström, "Bending Bilayer Strips Built From Polyaniline For Artificial Electrochemical Muscles," *Smart Materials and Structures*, vol. 2, pp. 16., Jan. 22, 1993.

Pelrine R. E., et al.: "Electrostriction of Polymer Dielectrics with Compliant Electrodes As a Means of Actuation", Sensors and Actuators A., Elsevier Sequoia S.A., Lausanne, Ch, vol. 64, No. 1, 1998, pp. 77-85, XP004102141, ISSN: 0924-4247.

Pelrine, R, R. Kornbluh, J. Joseph, and S. Chiba, "Electrostriction of Polymer Films for Microactuators," *Proc. IEEE Tenth Annual International Workshop on Micro Electro Mechanical Systems*, Nagoya, Japan, Jan. 26-30, 1997, pp. 238-243.

Pelrine, R., and J. Joseph, *FY 1992 Final Report on Artificial Muscle for Small Robots*, ITAD-3393-FR-93-063, SRI International, Menlo Park, California, Mar. 1993.

Pelrine, R., and J. Joseph. 1994. *FY 1993 Final Report on Artificial Muscle for Small Robots*, ITAD-4570-FR-94-076, SRI International, Menlo Park, California.

Pelrine, R., J. Eckerle, and S. Chiba, "Review of Artificial Muscle Approaches," invited paper, in *Proc. Third International Symposium on Micro Machine and Human Science*, Nagoya, Japan, Oct. 14-16, 1992.

Pelrine, R., R. Kornbluh, and G. Kofod, "High Strain Actuator Materials Based on Dielectric Elastomers," submitted to *Advanced Materials* (May 2000).

Pelrine, R., R. Kornbluh, and J. Joseph, FY 1996 *Final Report on Artificial Muscle for Small Robots*, ITAD-7228-FR-97-058, SRI International, Menlo Park, California, 1997.

Pelrine, R., R. Kornbluh, and J. Joseph, FY 1997 *Final Report on Artificial Muscle for Small Robots*, ITAD-1612-FR-98-041, SRI International, Menlo Park, California, 1998.

Pelrine, R., R. Kornbluh, and J. Joseph, FY 1998 *Final Report on Artificial Muscle for Small Robots*, ITAD-3482-FR-99-36, SRI International, Menlo Park, California, 1999.

Pelrine, R., R. Kornbluh, and J. Joseph, FY 1999 *Final Report on Artificial Muscle for Small Robots*, ITAD-10162-FR-00-27, SRI International, Menlo Park, California, 2000.

Pelrine, R., R. Kornbluh, and J. Joseph, "Electrostriction of Polymer Dielectrics with Compliant Electrodes as a Means of Actuation," *Sensors and Actuators A: Physical*, vol. 64, 1998, pp. 77-85.

Pelrine, R., R. Kornbluh, and J. Joseph, *FY 1994 Final Report on Artificial Muscle for Small Robots*, ITAD-5782-FR-95-050, SRI International, Menlo Park, California, 1995.

Pelrine, R., R. Kornbluh, and J. Joseph, *FY 1995 Final Report on Artificial Muscle for Small Robots*, ITAD-7071 FR-96-047, SRI International, Menlo Park, California, 1996.

Pelrine, R., R. Kornbluh, Q. Pei, and J. Joseph, "High Speed Electrically Actuated Elastomers with Over 100% Strain," *Science*, vol. 287, No. 5454, pp. 1-21, 2000.

Pelrine, R., R. Kornbluh, Q. Pei, and J. Joseph. "High-Speed Electrically Actuated Elastomers with Strain Greater Than 100%", *Science*, Reprint Series, Feb. 4 2000, vol. 287, pp. 836-839.

Pelrine, R., Roy Kornbluh, Jose Joseph, Qibing Pei, Seiki Chiba "Recent Progress in Artificial Muscle Micro Actuators,", SRI International, Tokyo, 1999 MITI/NEEDOIMNIC, 1999.

Piezoflex™ PVDF Polymer Sensors, http://www.airmar.com/piezo/pvdf.htm, Jun. 6, 2001.

R. Pelrine and Kornbluh, R., and. 1995. "*Dexterous Multiarticulated Manipulator with Electrostrictive Polymer Artificial Muscle Actuator*," EMU 95-023, SRI International, Menlo Park, California, Apr. 28, 1995.

Ron Pelrine, Roy Kornbluh, Qibing Pei, Jose Joseph: "High-Speed ElectricallyActuated Elastomers With Strain Greater Than 100%" Science, vol. 287, Feb. 4, 2000, pp. 836-839, XP002288990, USA.

Scheinbeim, J., B. Newman, Z. Ma, and J. Lee, "Electrostrictive Response of Elastomeric Polymers," *ACS Polymer Preprints*, 33(2), pp. 385-386, 1992.

Schlaberg, H. I., and J. S. Duffy, "Piezoelectric Polymer Composite Arrays for Ultrasonic Medical Imaging Applications," *Sensors and Actuators*, A 44, pp. 111-117, Feb. 22, 1994.

Shahinpoor, M., "Micro-electro-mechanics of Ionic Polymer Gels as Electrically Controllable Artificial Muscles," *J. Intelligent Material Systems and Structures*, vol. 6, pp. 307-314, May 1995.

Shkel, Y., and D. Klingenberg, "Material Parameters for Electrostriction," *J Applied Physics*, vol. 80(8), pp. 4566-4572, Oct. 15, 1996.

Smela, E., O. Inganäs, and I. Lundström, "Controlled Folding of Micrometer-size Structures," *Science*, vol. 268, pp. 1735-1738 (Jun. 23, 1995).

Smela, E., O. Inganäs, Q. Pei, and I. Lundström, "Electrochemical Muscles: Micromachining Fingers and Corkscrews, "*Advanced Materials*, vol. 5, No. 9, pp. 630-632, Sep. 1993.

Su, J., Q. M. Zhang, C. H. Kim, R. Y. Ting, and R. Capps, "Effects of Transitional Phenomena on the Electric Field induced Strain-electrostrictive Response of a Segmented Polyurethane Elastomer," pp. 1363-1370, Jan. 20, 1997.

Su, J., Z. Ounaies, J. S. Harrison, Y. Bara-Cohen and S. Leary, "Electromechanically Active Polymer Blends for Actuation," Proceedings of the 7th SPIE Symposium on Smart Structures and Materials-Electroactive Polymers and Devices (EAPAD) Conference, Mar. 6-8, 2000, Newport Beach, California, USA, pp. 65-72.

T. B. Nguyen, C. K. DeBolt, Shastri, S. V., and A. Mann, "Advanced Robotic Search," in ONR Ocean, Atmosphere, and Space Fiscal Year 1999 Annual Reports (Dec. 1999).

Technology, http://www.micromuscle.com/html/technology.html, Jun. 6, 2001.

Tobushi, H., S. Hayashi, and S. Kojima, "Mechanical Properties of Shape Memory Polymer of Polyurethane Series," in *JSME International Journal*, Series I, vol. 35, No. 3, 1992.

Treloar, L.R.G, "Mechanics of Rubber Elasticity," *J Polymer Science, Polymer Symposium*, No. 48, pp. 107-123, 1974.

Uchino, K. 1986. "Electrostrictive Actuators: Materials and Applications," *Ceramic Bulletin*, 65(4), pp. 647-652, 1986.

Wade, W. L., Jr., R. J. Mammone and M. Binder, "Increased Dielectric Breakdown Strengths Of Melt-Extruded Polyporpylene Films," *Polymer*, vol. 34, No. 5, pp. 1093-1094 (1993).

Wax, S. G. and R. R. Sands, "Electroactive Polymer Actuators and Devices," Proceedings of the SPIE International Symposium on Smart Structures and Materials: Electro-Active Polymer Actuators and Devices, Mar. 1-2, 1999, Newport Beach, California, USA., pp. 2-10.

Winters, J., "Muscle as an Actuator for Intelligent Robots", Robotics Research: Trans. Robotics International of SME, Scottsdale, AZ (Aug. 18-21, 1986).

Yam, P., "Plastics Get Wired", *Scientific American*, vol. 273, pp. 82-87, Jul. 1995.

Zhang, Q. M., V. Bharti, Z.-Y. Cheng, T.-B. Xu, S. Wang, T. S. Ramotowski, F. Tito and R. Ting, "Electromechanical Behavior of Electroactive P(VDF-TrFE) Copolymers," Proceedings of the SPIE International Symposium on Smart Structures and Materials: Electro-Active Polymer Actuators and Devices, Mar. 1-2, 1999, Newport Beach, California, USA., pp. 134-139.

Zhang, Q. M., Z.-Y. Cheng, V. Bharti, T.-B. Xu, H. Xu, T. Mai, and S. J. Gross, "Piezoelectric and Electrostrictive Polymeric Actuator Materials," Proceedings of the 7th SPIE Symposium on Smart Structures and Materials-Electroactive Polymers and Devices (EAPAD) Conference, Mar. 6-8, 2000, Newport Beach, California, USA, pp. 34-50.

Zhang, Q., V. Bharti, and X. Zhao, "Giant Electrostriction and Relaxor Ferroelectric Behavior in Electron-irradiated Poly(vinylidene fluoride-trifluoroethylene) Copolymer," *Science*, vol. 280, pp. 2101-2104 (Jun. 26, 1998)

Zhenyi, M., J.I. Scheinbeim, J.W. Lee, and B.A. Newman. 1994. "High Field Electrostrictive Response of Polymers," *Journal of Polymer Sciences, Part B-Polymer Physics*, vol. 32, pp. 2721-2731, 1994.

Puers et al, "A Capacitive Pressure Sensor with Low Impedance Output and Active Suppression of Parasitic Effects," Sensors and Actuators, A21-A23 (1990) 108-114.

Robert Puers, "Capacitive sensors: when and how to use them," Sensors and Actuators A, 37-38 (1993) 93-105.

Seoul et al., "Electrospinning of Poly(vinylidene fluoride). Dimethylformamide Solutions with Carbon Nanotubes," Department of Textile Engineering, Inha University, Mar. 31, 2003.

Pelrine et al., "Electrostrictive Polymer Artificial Muscle Actuators," May 1998, Proc. of the 1998 IEEE Conf. on Robotics & Automation, 2147-2154.

MONOLITHIC ELECTROACTIVE POLYMERS

CROSS-REFERENCE TO RELATED APPLICATIONS

This application is a continuation and claims priority under 35 USC §120 from co-pending U.S. patent application Ser. No. 11/375,930 filed Mar. 14, 2006; the patent application Ser. No. 11/375,930 is a divisional of and claimed priority under U.S.C. §120 from U.S. patent application Ser. No. 10/393,506, filed Mar. 18, 2003 (now U.S. Pat. No. 7,064,472 issued Jun. 20, 2006) and entitled, "Electroactive Polymer Devices for Moving Fluid"; the '506 patent application is a continuation-in-part and claimed priority from U.S. patent application Ser. No. 09/619,847, now U.S. Pat. No. 6,812,624 entitled "Improved Electroactive Polymers," filed Jul. 20, 2000 and issued Nov. 2, 2004, which is incorporated herein by reference in its entirety for all purposes which claimed priority a) under 35 U.S.C. §119(e) from U.S. Provisional Patent Application No. 60/144,556 filed Jul. 20, 1999, naming Pelrine et al. as inventors, and titled "High-speed Electrically Actuated Polymers and Method of Use", which is incorporated by reference herein for all purposes, b) under 35 U.S.C. §119(e) from U.S. Provisional Patent Application No. 60/153,329 filed Sep. 10, 1999, naming Pelrine et al. as inventors, and titled "Electrostrictive Polymers As Microactuators", which is incorporated by reference herein for all purposes, c) under 35 U.S.C. §119(e) from U.S. Provisional Patent Application No. 60/161,325 filed Oct. 25, 1999, naming Pelrine et al. as inventors, and titled "Artificial Muscle Microactuators", which is incorporated by reference herein for all purposes, d) under 35 U.S.C. §119(e) from U.S. Provisional Patent Application No. 60/181,404 filed Feb. 9, 2000, naming Kornbluh et al. as inventors, and titled "Field Actuated Elastomeric Polymers", which is incorporated by reference herein for all purposes, e) under 35 U.S.C. §119(e) from U.S. Provisional Patent Application No. 60/187,809 filed Mar. 8, 2000, naming Pelrine et al. as inventors, and titled "Polymer Actuators and Materials", which is incorporated by reference herein for all purposes, f) under 35 U.S.C. §119(e) from U.S. Provisional Patent Application No. 60/192,237 filed Mar. 27, 2000, naming Kornbluh et al. as inventors, and titled "Polymer Actuators and Materials II", which is incorporated by reference herein for all purposes, and g) under 35 U.S.C. §119(e) from U.S. Provisional Patent Application No. 60/184,217 filed Feb. 23, 2000, naming Pelrine et al. as inventors, and titled "Electroelastomers and their use for Power Generation", which is incorporated by reference herein for all purposes; and the '506 patent application is a continuation-in-part and claims priority from U.S. patent application Ser. No. 09/779,203, now U.S. Pat. No. 6,664,718, filed Feb. 7, 2001 and issued Dec. 16, 2003, by Pelrine et al., and entitled, "Monolithic Electroactive Polymers," which claimed priority under 35 U.S.C. §119(e) from U.S. Provisional Patent Application No. 60/181,404, filed Feb. 9, 2000, which is incorporated by reference for all purposes

U.S. GOVERNMENT RIGHTS

This application was made in part with government support under contract number N00014-96-C-0026 awarded by the Office of Naval Research; this application was also made in part with government support under contract number DAAG55-98-K-001 awarded by the United States Army Research Office and Defense Advanced Research Project Agency. The government has certain rights in the invention.

BACKGROUND OF THE INVENTION

The present invention relates generally to electroactive polymers that convert between electrical energy and mechanical energy. More particularly, the present invention relates to electroactive polymers having multiple active areas. The present invention also relates to methods of actuating electroactive polymers having multiple active areas.

In many applications, it is desirable to convert between electrical energy and mechanical energy. Exemplary applications requiring conversion from electrical to mechanical energy include robotics, pumps, speakers, general automation, disk drives and prosthetic devices. These applications include one or more actuators that convert electrical energy into mechanical work—on a macroscopic or microscopic level. Common actuator technologies, such as electromagnetic motors and solenoids, are not suitable for many of these applications, e.g., when the required device size is small (e.g., micro or mesoscale machines) or the weight or complexity must be minimized. Exemplary applications requiring conversion from mechanical to electrical energy include sensors and generators. These applications include one or more transducers that convert mechanical energy into electrical energy. Common electric generator technologies, such as electromagnetic generators, are not suitable for many of these applications, e.g., when the required device size is small (e.g., in a person's shoe). These transducer technologies are also not ideal when a large number of devices must be integrated into a single structure or under various performance conditions such as when high power density output is required at relatively low frequencies.

Several 'smart materials' have been used to convert between electrical and mechanical energy with limited success. These smart materials include piezoelectric ceramics, shape memory alloys and magnetostrictive materials. However, each smart material has a number of limitations that prevent its broad usage. Certain piezoelectric ceramics, such as lead zirconium titanate (PZT), have been used to convert electrical to mechanical energy. While having suitable efficiency for a few applications, these piezoelectric ceramics are typically limited to a strain below about 1.6 percent and are often not suitable for applications requiring greater strains than this. In addition, the high density of these materials often eliminates them from applications requiring low weight. Irradiated polyvinylidene fluoride (PVDF) is an electroactive polymer reported to have a strain of up to 4 percent when converting from electrical to mechanical energy. Similar to the piezoelectric ceramics, PVDF is often not suitable for applications requiring strains greater than 4 percent. Shape memory alloys, such as nitinol, are capable of large strains and force outputs. These shape memory alloys have been limited from broad use due to unacceptable energy efficiency, poor response time and prohibitive cost.

In addition to the performance limitations of piezoelectric ceramics and irradiated PVDF, their fabrication often presents a barrier to acceptability. Single crystal piezoelectric ceramics must be grown at high temperatures coupled with a very slow cooling down process. Irradiated PVDF must be exposed to an electron beam for processing. Both these processes are expensive and complex and may limit acceptability of these materials.

In view of the foregoing, alternative devices that convert between electrical and mechanical energy would be desirable.

SUMMARY OF THE INVENTION

In one aspect, the present invention relates to polymers that convert between electrical and mechanical energy. When a voltage is applied to electrodes contacting an electroactive polymer, the polymer deflects. This deflection may be used to do mechanical work. Similarly, when a previously charged electroactive polymer deflects, the electric field in the material is changed. The change in electric field may be used to produce electrical energy. An active area is a portion of a polymer having sufficient electrostatic force to enable deflection of the portion and/or sufficient deflection to enable a change in electrostatic force or electric field. The present invention relates to transducers and devices comprising multiple active areas. The invention also relates to methods for actuating one or more active areas.

In another aspect, the invention relates to a transducer for converting between electrical energy and mechanical energy. The transducer comprises an electroactive polymer having a plurality of active areas. The plurality of active areas comprise a first active area having at least two first active area electrodes and a first portion of the electroactive polymer arranged in a manner which causes the first portion to deflect in response to a change in electric field provided by the at least two first active area electrodes and/or arranged in a manner which causes a change in electric field in response to deflection of the first portion. The plurality of active areas also comprise a second active area having at least two second active area electrodes and a second portion of the electroactive polymer arranged in a manner which causes the second portion to deflect in response to a change in electric field provided by the at least two second active area electrodes and/or arranged in a manner which causes a change in electric field in response to deflection of the second portion.

In yet another aspect, the invention relates to a device for converting between electrical energy and mechanical energy. The device comprises an electroactive polymer having a plurality of active areas. The plurality of active areas comprise a first active area having at least two first active area electrodes and a first portion of the electroactive polymer arranged in a manner which causes the first portion to deflect in response to a change in electric field provided by the at least two first active area electrodes and/or arranged in a manner which causes a change in electric field in response to deflection of the first portion. The plurality of active areas also comprise a second active area having at least two second active area electrodes and a second portion of the electroactive polymer arranged in a manner which causes the second portion to deflect in response to a change in electric field provided by the at least two second active area electrodes and/or arranged in a manner which causes a change in electric field in response to deflection of the second portion. The device also comprises a substantially rigid member coupled to a third portion of the electroactive polymer.

In yet another aspect, the invention relates to a method for using an electroactive polymer having a plurality of active areas. The electroactive polymer comprises a first active area and a second active area, the first active area having at least two first active area electrodes and a first portion of the electroactive polymer, the second active area having at least two second active area electrodes and a second portion of the electroactive polymer. The method comprises providing a change in electric field to the at least two first active area electrodes. The method also comprises providing a change in electric field to the at least two second active area electrodes.

In still another aspect, the invention relates to a transducer for converting between electrical energy and mechanical energy. The transducer comprises an electroactive polymer having a plurality of active areas. The plurality of active areas comprise a first active area having a first electrode, a common electrode, and a first portion of the electroactive polymer arranged in a manner which causes the first portion to deflect in response to a change in electric field provided by the first electrode and the common electrode and/or arranged in a manner which causes a change in electric field in response to deflection of the first portion. The plurality of active areas also comprise a second active area having a second electrode, the common electrode, and a second portion of the electroactive polymer arranged in a manner which causes the second portion to deflect in response to a change in electric field provided by the second electrode and the common electrode and/or arranged in a manner which causes a change in electric field in response to deflection of the second portion.

In yet another aspect, the invention relates to a transducer for converting between electrical energy and mechanical energy. The transducer comprises an electroactive polymer having a plurality of active areas. The plurality of active areas comprise a first active area having at least two first active area electrodes and a first portion of the electroactive polymer arranged in a manner which causes the first portion to deflect in response to a change in electric field provided by the at least two first active area electrodes and/or arranged in a manner which causes a change in electric field in response to deflection of the first portion. The plurality of active areas also comprise a second active area having at least two second active area electrodes and a second portion of the electroactive polymer arranged in a manner which causes the second portion to deflect in response to a change in electric field provided by the at least two second active area electrodes and/or arranged in a manner which causes a change in electric field in response to deflection of the second portion.

In still another aspect, the invention relates to a device for converting between electrical energy and mechanical energy. The device comprises an electroactive polymer having a plurality of active areas. The plurality of active areas comprise a first active area having at least two first active area electrodes and a first portion of the electroactive polymer arranged in a manner which causes the first portion to deflect in response to a change in electric field provided by the at least two first active area electrodes and/or arranged in a manner which causes a change in electric field in response to deflection of the first portion. The plurality of active areas also comprise a second active area having at least two second active area electrodes and a second portion of the electroactive polymer arranged in a manner which causes the second portion to deflect in response to a change in electric field provided by the at least two second active area electrodes and/or arranged in a manner which causes a change in electric field in response to deflection of the second portion. The device further comprises a substantially rigid member having a first portion and a second portion. The first portion of the substantially rigid member coupled to a third portion of the electroactive polymer. The second portion of the substantially rigid member capable of motion assisted by deflection of the first portion of the polymer in response to a change in electric field provided by the at least two first active area electrodes and/or capable of motion that causes a change in electric field in the first portion of the polymer. The device additionally comprises a frame coupled to a fourth portion of the polymer.

These and other features and advantages of the present invention will be described in the following description of the invention and associated figures.

DETAILED DESCRIPTION OF THE PREFERRED EMBODIMENTS

Figure 1A:
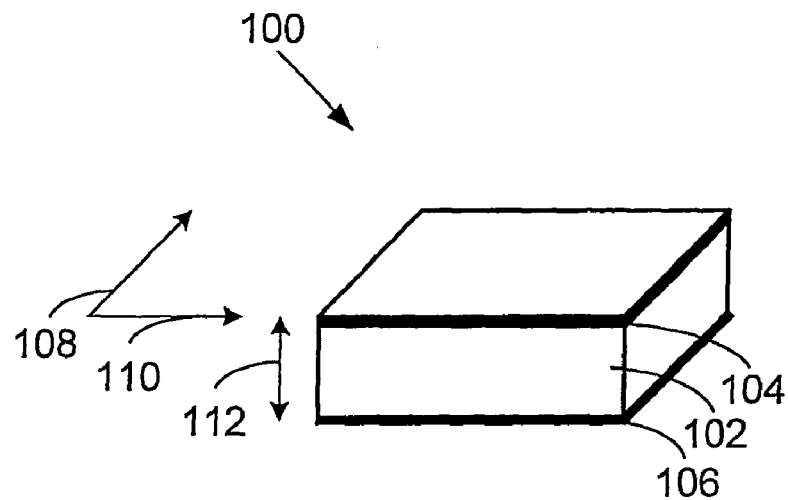
FIGS. 1A and 1B illustrate a top view of a transducer portion before and after application of a voltage, respectively, in accordance with one embodiment of the present invention.

The present invention is described in detail with reference to a few preferred embodiments as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

1. OVERVIEW

Electroactive polymers convert between mechanical and electrical energy. In one aspect, the present invention relates to electroactive polymer transducers that comprise multiple active areas. The multiple active areas may be arranged on a single polymer. The ability to arrange multiple active areas on a single polymer allows for numerous transducer configurations. The multiple active areas may be used in a variety of ways. The ability to use these multiple active areas independently increases electroactive polymer flexibility in converting between electrical and mechanical energy and allows the polymers to be used in many new applications. For example, multiple active areas on a single electroactive polymer may be independently actuated to deflect a portion of the polymer along a two-dimensional path. The two-dimensional path may be a circular path used in driving a crank in a motor. Combining different ways to arrange active areas on a polymer, different ways to constrain a polymer, scalability of electroactive polymers to both micro and macro levels, and different polymer orientations (e.g., rolling or stacking individual polymer layers) permits a broad range of designs for actuators, motors, sensors, generators, and other transducer devices. These devices find use in a wide range of applications.

For ease of understanding, the present invention is mainly described and shown by focusing on a single direction of energy conversion. More specifically, the present invention focuses on converting electrical energy into mechanical energy, i.e., when a transducer is operating in an actuator. However, in all the figures and discussions for the present invention, it is important to note that the polymers and devices may convert between electrical energy and mechanical energy bi-directionally. Thus, any of the polymer materials, polymer configurations, transducers, and devices described herein are also a transducer for converting mechanical energy to electrical energy (a generator). Similarly, any of the exemplary electrodes described herein may be used with a generator of the present invention. Typically, a generator of the present invention comprises a polymer arranged in a manner that causes a change in electric field in response to deflection of a portion of the polymer. The change in electric field, along with changes in the polymer dimension in the direction of the field, produces a change in voltage, and hence a change in electrical energy.

Thus, polymers and transducers of the present invention may be used as an actuator to convert from electrical to mechanical energy or a generator to convert from mechanical to electrical energy. For a transducer having a substantially constant thickness, one mechanism for differentiating the performance of the transducer, or a portion of the transducer associated with a single active area, as being an actuator or a generator is in the change in net area orthogonal to the thickness associated with the polymer deflection. For these transducers or active areas, when the deflection causes the net area of the transducer/active area to decrease and there is charge on the electrodes, the transducer/active area is converting from mechanical to electrical energy and acting as a generator. Conversely, when the deflection causes the net area of the transducer/active area to increase and charge is on the electrodes, the transducer/active area is converting electrical to mechanical energy and acting as an actuator. The change in area in both cases corresponds to a reverse change in film thickness, i.e. the thickness contracts when the planar area expands, and the thickness expands when the planar area contracts. Both the change in area and change in thickness determine the amount of energy that is converted between electrical and mechanical. Since the effects due to a change in area and corresponding change in thickness are complementary, only the change in area will be discussed herein for sake of brevity. In addition, although deflection of an electroactive polymer will primarily be discussed as a net increase in area of the polymer when the polymer is being used in an actuator to produce mechanical energy, it is understood that in some cases (i.e. depending on the loading), the net area may decrease to produce mechanical work. Thus, devices of the present invention may include both actuator and generator modes, depending on how the polymer is arranged and applied.

2. GENERAL STRUCTURE OF ELECTROACTIVE POLYMERS

The transformation between electrical and mechanical energy in devices of the present invention is based on energy conversion of one or more active areas of an electroactive polymer. Electroactive polymers deflect when actuated by electrical energy. To help illustrate the performance of an electroactive polymer in converting electrical energy to mechanical energy, FIG. 1A illustrates a top perspective view of a transducer portion 100 in accordance with one embodiment of the present invention. The transducer portion 100 comprises an electroactive polymer 102 for converting between electrical energy and mechanical energy. In one embodiment, an electroactive polymer refers to a polymer that acts as an insulating dielectric between two electrodes and may deflect upon application of a voltage difference between the two electrodes. Top and bottom electrodes 104 and 106 are attached to the electroactive polymer 102 on its top and bottom surfaces, respectively, to provide a voltage difference across a portion of the polymer 102. Polymer 102 deflects with a change in electric field provided by the top and bottom electrodes 104 and 106. Deflection of the transducer portion 100 in response to a change in electric field provided by the electrodes 104 and 106 is referred to as actuation. As polymer 102 changes in size, the deflection may be used to produce mechanical work.

Figure 1B:
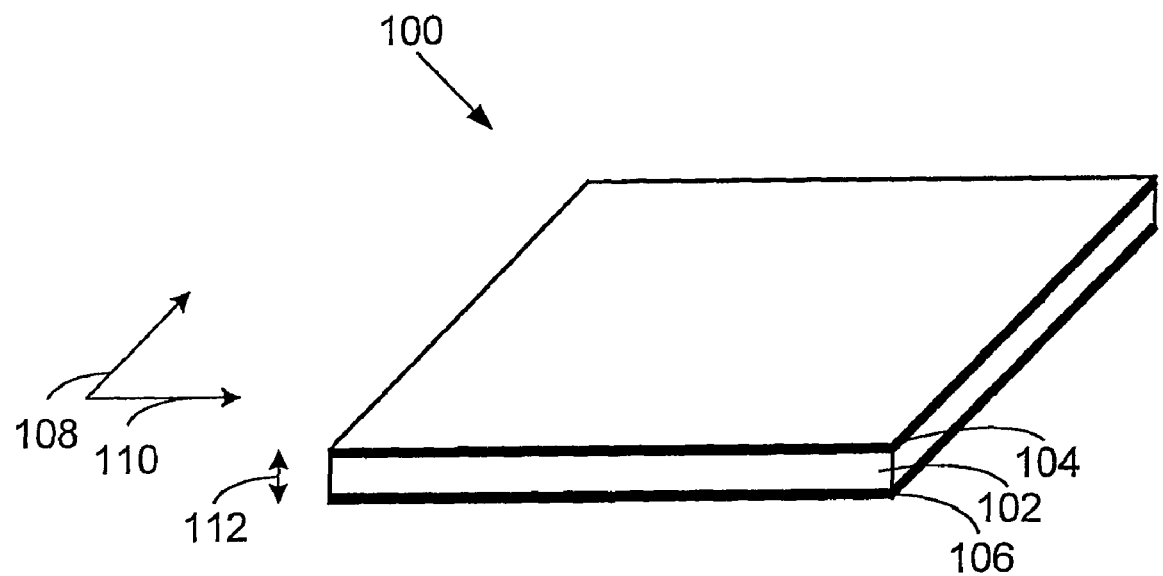

FIG. 1B illustrates a top perspective view of the transducer portion 100 including deflection in response to a change in electric field. In general, deflection refers to any displacement, expansion, contraction, torsion, linear or area strain, or any other deformation of a portion of the polymer 102. The change in electric field corresponding to the voltage difference applied to or by the electrodes 104 and 106 produces mechanical pressure within polymer 102. In this case, the unlike electrical charges produced by electrodes 104 and 106 attract each other and provide a compressive force between electrodes 104 and 106 and an expansion force on polymer 102 in planar directions 108 and 110, causing polymer 102 to compress between electrodes 104 and 106 and stretch in the planar directions 108 and 110.

In some cases, electrodes 104 and 106 cover a limited portion of polymer 102 relative to the total area of the polymer. This may be done to prevent electrical breakdown around the edge of polymer 102 or to achieve customized deflections for one or more portions of the polymer. As the term is used herein, an active area is defined as a portion of a transducer comprising polymer material 102 and at least two electrodes. When the active area is used to convert electrical energy to mechanical energy, the active area includes a portion of polymer 102 having sufficient electrostatic force to enable deflection of the portion. When the active area is used to convert mechanical energy to electrical energy, the active area includes a portion of polymer 102 having sufficient deflection to enable a change in electrostatic energy. As will be described below, a polymer of the present invention may have multiple active areas. In some cases, polymer 102 material outside an active area may act as an external spring force on the active area during deflection. More specifically, polymer material outside the active area may resist active area deflection by its contraction or expansion. Removal of the voltage difference and the induced charge causes the reverse effects.

Electrodes 104 and 106 are compliant and change shape with polymer 102. The configuration of polymer 102 and electrodes 104 and 106 provides for increasing polymer 102 response with deflection. More specifically, as the transducer portion 100 deflects, compression of polymer 102 brings the opposite charges of electrodes 104 and 106 closer and the stretching of polymer 102 separates similar charges in each electrode. In one embodiment, one of the electrodes 104 and 106 is ground.

In general, the transducer portion 100 continues to deflect until mechanical forces balance the electrostatic forces driving the deflection. The mechanical forces include elastic restoring forces of the polymer 102 material, the compliance of electrodes 104 and 106, and any external resistance provided by a device and/or load coupled to the transducer portion 100, etc. The deflection of the transducer portion 100 as a result of the applied voltage may also depend on a number of other factors such as the polymer 102 dielectric constant and the size of polymer 102.

Electroactive polymers in accordance with the present invention are capable of deflection in any direction. After application of the voltage between electrodes 104 and 106, polymer 102 expands (stretches) in both planar directions 108 and 110. In some cases, polymer 102 is incompressible, e.g. has a substantially constant volume under stress. For an incompressible polymer 102, polymer 102 decreases in thickness as a result of the expansion in the planar directions 108 and 110. It should be noted that the present invention is not limited to incompressible polymers and deflection of the polymer 102 may not conform to such a simple relationship.

Application of a relatively large voltage difference between electrodes 104 and 106 on the transducer portion 100 shown in FIG. 1A will cause transducer portion 100 to change to a thinner, larger area shape as shown in FIG. 1B. In this manner, the transducer portion 100 converts electrical energy to mechanical energy. The transducer portion 100 may also be used to convert mechanical energy to electrical energy.

FIGS. 1A and 1B may be used to show one manner in which the transducer portion 100 converts mechanical energy to electrical energy. For example, if the transducer portion 100 is mechanically stretched by external forces to a thinner, larger area shape such as that shown in FIG. 1B, and a relatively small voltage difference (less than that necessary to actuate the film to the configuration in FIG. 1B) is applied between electrodes 104 and 106, the transducer portion 100 will contract in area between the electrodes to a shape such as in FIG. 1A when the external forces are removed. Stretching the transducer refers to deflecting the transducer from its original resting position—typically to result in a larger net area between the electrodes, e.g. in the plane defined by directions 108 and 110 between the electrodes. The resting position refers to the position of the transducer portion 100 having no external electrical or mechanical input and may comprise any pre-strain in the polymer. Once the transducer portion 100 is stretched, the relatively small voltage difference is provided such that the resulting electrostatic forces are insufficient to balance the elastic restoring forces of the stretch. The transducer portion 100 therefore contracts, and it becomes thicker and has a smaller planar area in the plane defined by directions 108 and 110 (orthogonal to the thickness between electrodes). When polymer 102 becomes thicker, it separates electrodes 104 and 106 and their corresponding unlike charges, thus raising the electrical energy and voltage of the charge. Further, when electrodes 104 and 106 contract to a smaller area, like charges within each electrode compress, also raising the electrical energy and voltage of the charge. Thus, with different charges on electrodes 104 and 106, contraction from a shape such as that shown in FIG. 1B to one such as that shown in FIG. 1A raises the electrical energy of the charge. That is, mechanical deflection is being turned into electrical energy and the transducer portion 100 is acting as a generator.

In some cases, the transducer portion 100 may be described electrically as a variable capacitor. The capacitance decreases for the shape change going from that shown in FIG. 1B to that shown in FIG. 1A. Typically, the voltage difference between electrodes 104 and 106 will be raised by contraction. This is normally the case, for example, if additional charge is not added or subtracted from electrodes 104 and 106 during the contraction process. The increase in electrical energy, U, may be illustrated by the formula $U=0.5\ Q^2/C$, where Q is the amount of positive charge on the positive electrode and C is the variable capacitance which relates to the intrinsic dielectric properties of polymer 102 and its geometry. If Q is fixed and C decreases, then the electrical energy U increases. The increase in electrical energy and voltage can be recovered or used in a suitable device or electronic circuit in electrical communication with electrodes 104 and 106. In addition, the transducer portion 100 may be mechanically coupled to a mechanical input that deflects the polymer and provides mechanical energy.

The transducer portion 100 will convert mechanical energy to electrical energy when it contracts. Some or all of the charge and energy can be removed when the transducer portion 100 is fully contracted in the plane defined by directions 108 and 110. Alternatively, some or all of the charge and energy can be removed during contraction. If the electric field pressure in the polymer increases and reaches balance with the mechanical elastic restoring forces and external load during contraction, the contraction will stop before full contraction, and no further elastic mechanical energy will be converted to electrical energy. Removing some of the charge and stored electrical energy reduces the electrical field pressure, thereby allowing contraction to continue. Thus, removing some of the charge may further convert mechanical energy to electrical energy. The exact electrical behavior of the transducer portion 100 when operating as a generator depends on any electrical and mechanical loading as well as the intrinsic properties of polymer 102 and electrodes 104 and 106.

In one embodiment, electroactive polymer 102 is pre-strained. Pre-strain of a polymer may be described, in one or more directions, as the change in dimension in a direction after pre-straining relative to the dimension in that direction before pre-straining. The pre-strain may comprise elastic deformation of polymer 102 and be formed, for example, by stretching the polymer in tension and fixing one or more of the edges while stretched. For many polymers, pre-strain improves conversion between electrical and mechanical energy. The improved mechanical response enables greater mechanical work for an electroactive polymer, e.g., larger deflections and actuation pressures. In one embodiment, pre-strain improves the dielectric strength of the polymer. In another embodiment, the pre-strain is elastic. After actuation, an elastically pre-strained polymer could, in principle, be unfixed and return to its original state. The pre-strain may be imposed at the boundaries using a rigid frame or may also be implemented locally for a portion of the polymer.

In one embodiment, pre-strain is applied uniformly over a portion of polymer 102 to produce an isotropic pre-strained polymer. By way of example, an acrylic elastomeric polymer may be stretched by 200 to 400 percent in both planar directions. In another embodiment, pre-strain is applied unequally in different directions for a portion of polymer 102 to produce an anisotropic pre-strained polymer. In this case, polymer 102 may deflect greater in one direction than another when actuated. While not wishing to be bound by theory, it is believed that pre-straining a polymer in one direction may increase the stiffness of the polymer in the pre-strain direction. Correspondingly, the polymer is relatively stiffer in the high pre-strain direction and more compliant in the low pre-strain direction and, upon actuation, more deflection occurs in the low pre-strain direction. In one embodiment, the deflection in direction 108 of transducer portion 100 can be enhanced by exploiting large pre-strain in the perpendicular direction 110. For example, an acrylic elastomeric polymer used as the transducer portion 100 may be stretched by 100 percent in direction 108 and by 500 percent in the perpendicular direction 110. The quantity of pre-strain for a polymer may be based on the polymer material and the desired performance of the polymer in an application. Pre-strain suitable for use with the present invention is further described in commonly owned, copending U.S. patent application Ser. No. 09/619,848, which is incorporated by reference for all purposes.

Generally, after the polymer is pre-strained, it may be fixed to one or more objects. Each object is preferably suitably stiff to maintain the level of pre-strain desired in the polymer. The polymer may be fixed to the one or more objects according to any conventional method known in the art such as a chemical adhesive, an adhesive layer or material, mechanical attachment, etc. Transducers and pre-strained polymers of the present invention are not limited to any particular geometry or type of deflection. For example, the polymer and electrodes may be formed into any geometry or shape including tubes and rolls, stretched polymers attached between multiple rigid structures, stretched polymers attached across a frame of any geometry—including curved or complex geometries, across a frame having one or more joints, etc. Deflection of a transducer according to the present invention includes linear expansion and compression in one or more directions, bending, axial deflection when the polymer is rolled, deflection out of a hole provided in a substrate, etc. Deflection of a transducer may be affected by how the polymer is constrained by a frame or rigid structures attached to the polymer. In one embodiment, a flexible material that is stiffer in elongation than the polymer is attached to one side of a transducer induces bending when the polymer is actuated.

Materials suitable for use as a pre-strained polymer with the present invention may include any substantially insulating polymer or rubber (or combination thereof) that deforms in response to an electrostatic force or whose deformation results in a change in electric field. One suitable material is NuSil CF19-2186 as provided by NuSil Technology of Carpenteria, Calif. Other exemplary materials suitable for use as a pre-strained polymer include silicone elastomers, acrylic elastomers such as VHB 4910 acrylic elastomer as produced by 3M Corporation of St. Paul, Minn., polyurethanes, thermoplastic elastomers, copolymers comprising PVDF, pressure-sensitive adhesives, fluoroelastomers, polymers comprising silicone and acrylic moieties, and the like. Polymers comprising silicone and acrylic moieties may include copolymers comprising silicone and acrylic moieties, polymer blends comprising a silicone elastomer and an acrylic elastomer, for example. Combinations of some of these materials may also be used as the electroactive polymer in transducers of this invention.

Materials used as a pre-strained polymer may be selected based on one or more material properties such as a high electrical breakdown strength, a low modulus of elasticity—for large or small deformations, a high dielectric constant, etc. In one embodiment, the polymer is selected such that is has an elastic modulus below 100 MPa. In another embodiment, the polymer is selected such that is has a maximum actuation pressure between about 0.05 MPa and about 10 MPa, and preferably between about 0.3 MPa and about 3 MPa. In another embodiment, the polymer is selected such that is has a dielectric constant between about 2 and about 20, and preferably between about 2.5 and about 12. For some applications, an electroactive polymer is selected based on one or more application demands such as a wide temperature and/or humidity range, repeatability, accuracy, low creep, reliability and endurance.

An electroactive polymer layer in transducers of the present invention may have a wide range of thicknesses. In one embodiment, polymer thickness may range between about 1 micrometer and 2 millimeters. Polymer thickness may be reduced by stretching the film in one or both planar directions. In many cases, electroactive polymers of the present invention may be fabricated and implemented as thin films. Thicknesses suitable for these thin films may be below 50 micrometers.

Suitable actuation voltages for electroactive polymers, or portions thereof, may vary based on the material properties of the electroactive polymer, such as the dielectric constant, as well as the dimensions of the polymer, such as the thickness of the polymer film For example, actuation electric fields used to actuate polymer 102 in FIG. 1A may range in magnitude from about 0 V/m to about 440 MV/m. Actuation electric fields in this range may produce a pressure in the range of about 0 Pa to about 10 MPa. In order for the transducer to produce greater forces, the thickness of the polymer layer may be increased. Actuation voltages for a particular polymer may be reduced by increasing the dielectric constant, decreasing the polymer thickness, and decreasing the modulus of elasticity, for example.

As electroactive polymers of the present invention may deflect at high strains, electrodes attached to the polymers should also deflect without compromising mechanical or electrical performance. Generally, electrodes suitable for use with the present invention may be of any shape and material provided that they are able to supply a suitable voltage to, or receive a suitable voltage from, an electroactive polymer. The voltage may be either constant or varying over time. In one embodiment, the electrodes adhere to a surface of the polymer. Electrodes adhering to the polymer are preferably compliant and conform to the changing shape of the polymer. Correspondingly, the present invention may include compliant electrodes that conform to the shape of an electroactive polymer to which they are attached. The electrodes may be only applied to a portion of an electroactive polymer and define an active area according to their geometry. Several examples of electrodes that only cover a portion of an electroactive polymer will be described in further detail below.

Various types of electrodes suitable for use with the present invention are described in commonly owned, copending U.S. patent application Ser. No. 09/619,848, which was previously incorporated by reference above. Electrodes described therein and suitable for use with the present invention include structured electrodes comprising metal traces and charge distribution layers, textured electrodes comprising varying out of plane dimensions, conductive greases such as carbon greases or silver greases, colloidal suspensions, high aspect ratio conductive materials such as carbon fibrils and carbon nanotubes, and mixtures of ionically conductive materials.

Materials used for electrodes of the present invention may vary. Suitable materials used in an electrode may include graphite, carbon black, colloidal suspensions, thin metals including silver and gold, silver filled and carbon filled gels and polymers, and ionically or electronically conductive polymers. In a specific embodiment, an electrode suitable for use with the present invention comprises 80 percent carbon grease and 20 percent carbon black in a silicone rubber binder such as Stockwell RTV60-CON as produced by Stockwell Rubber Co. Inc. of Philadelphia, Pa. The carbon grease is of the type such as NyoGel 756G as provided by Nye Lubricant Inc. of Fairhaven, Mass. The conductive grease may also be mixed with an elastomer, such as silicon elastomer RTV 118 as produced by General Electric of Waterford, N.Y., to provide a gel-like conductive grease.

It is understood that certain electrode materials may work well with particular polymers and may not work as well for others. By way of example, carbon fibrils work well with acrylic elastomer polymers while not as well with silicone polymers. For most transducers, desirable properties for the compliant electrode may include one or more of the following: low modulus of elasticity, low mechanical damping, low surface resistivity, uniform resistivity, chemical and environmental stability, chemical compatibility with the electroactive polymer, good adherence to the electroactive polymer, and the ability to form smooth surfaces. In some cases, a transducer of the present invention may implement two different types of electrodes, e.g. a different electrode type for each active area or different electrode types on opposing sides of a polymer.

Electronic drivers are typically connected to the electrodes. The voltage provided to electroactive polymer will depend upon specifics of an application. In one embodiment, a transducer of the present invention is driven electrically by modulating an applied voltage about a DC bias voltage. Modulation about a bias voltage allows for improved sensitivity and linearity of the transducer to the applied voltage. For example, a transducer used in an audio application may be driven by a signal of up to 200 to 1000 volts peak to peak on top of a bias voltage ranging from about 750 to 2000 volts DC.

3. MULTIPLE ACTIVE AREAS

Figure 1C:
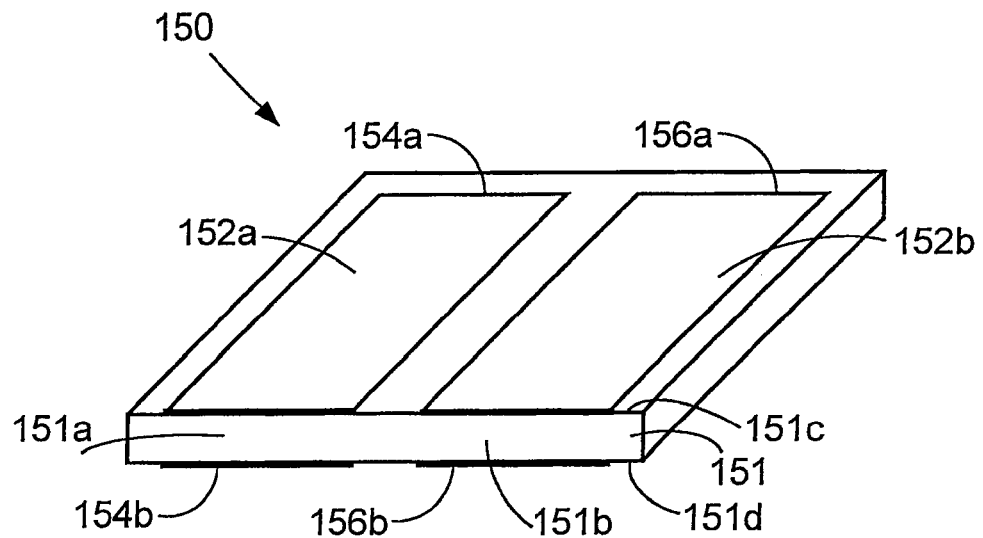
FIG. 1C illustrates a monolithic transducer comprising a plurality of active areas in accordance with one embodiment of the present invention.

In accordance with the present invention, the term "monolithic" is used herein to refer to electroactive polymers, transducers, and devices comprising a plurality of active areas. FIG. 1C illustrates a monolithic transducer 150 comprising a plurality of active areas in accordance with one embodiment of the present invention. The monolithic transducer 150 converts between electrical energy and mechanical energy. The monolithic transducer 150 comprises an electroactive polymer 151 having two active areas 152a and 152b. Polymer 151 may be held in place using, for example, a rigid frame (not shown) attached at the edges of the polymer.

The active area 152a has top and bottom electrodes 154a and 154b that are attached to polymer 151 on its top and bottom surfaces 151c and 151d, respectively. The electrodes 154a and 154b provide a voltage difference across a portion 151a of the polymer 151. The portion 151a deflects with a change in electric field provided by the electrodes 154a and 154b. The portion 151a comprises the polymer 151 between the electrodes 154a and 154b and any other portions of the polymer 151 having sufficient electrostatic force to enable deflection upon application of voltages using the electrodes 154a and 154b. When the device 150 is used as a generator to convert from electrical energy to mechanical energy, deflection of the portion 151a causes a change in electric field in the portion 151a that is received as a change in voltage difference by the electrodes 154a and 154b.

The active area 152b has top and bottom electrodes 156a and 156b that are attached to the polymer 151 on its top and bottom surfaces 151c and 151d, respectively. The electrodes 156a and 156b provide a voltage difference across a portion 151b of the polymer 151. The portion 151b deflects with a change in electric field provided by the electrodes 156a and 156b. The portion 151b comprises the polymer 151 between the electrodes 156a and 156b and any other portions of the polymer 151 having sufficient stress induced by the electrostatic force to enable deflection upon application of voltages using the electrodes 156a and 156b. When the device 150 is used as a generator to convert from electrical energy to mechanical energy, deflection of the portion 151b causes a change in electric field in the portion 151b that is received as a change in voltage difference by the electrodes 156a and 156b.

The active areas for monolithic polymers and transducers of the present invention may be flexibly arranged. In one embodiment, active areas in a polymer are arranged such that the elasticity of the active areas is balanced. In another embodiment, a transducer of the present invention comprises a plurality of symmetrically arranged active areas. While one embodiment of present invention will now be described as a device, those skilled in the art will recognize that the present invention encompasses methods having as steps the actions performed by various parts of the device described below.

Figure 1D:
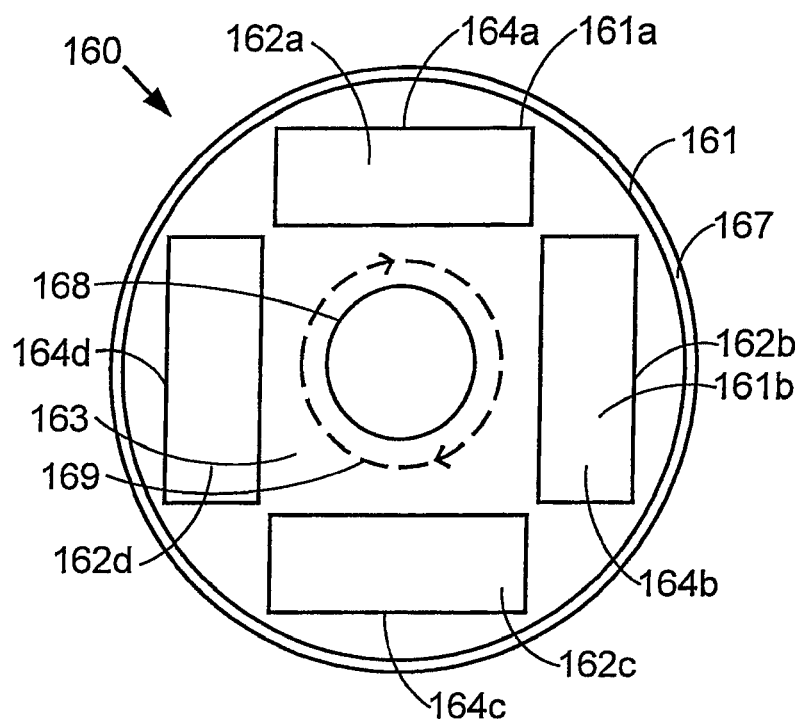
FIG. 1D illustrates a device comprising a plurality of symmetrically arranged electrodes in accordance with a specific embodiment of the present invention.

FIG. 1D illustrates a monolithic device 160 comprising a plurality of symmetrically arranged active areas in accordance with a specific embodiment of the present invention. The device 160 comprises a monolithic transducer comprising four active areas 162a-d. Each of the active areas 162a-d comprises top and bottom electrodes 164a-d attached to a polymer 161 on its top and bottom surfaces, respectively (only electrodes 164a-d on the facing surface of the polymer 161 are illustrated). The electrodes 164a-d each provide a voltage difference across a portion of the polymer 161. The electrodes 164a-d and their corresponding active areas 162a-d are symmetrically and radially arranged around a center point of the circular polymer 161. Correspondingly, the elasticity of the polymer material included in the active areas 162a-d is balanced.

A first active area 162a is formed with the two first active area electrodes 164a and a first portion of the electroactive polymer 161a. The portion 161a is arranged in a manner which causes the first portion 161a to deflect in response to a change in electric field provided by the first active area electrodes 164a. The portion 161a includes the polymer 161 between the electrodes 162a and any other portions of the polymer 161 having sufficient stresses induced by the electrostatic force to enable deflection upon application of voltages using the electrodes 162a. Similarly, a second active area 162c is formed with the two second active area electrodes 164c and a second portion of the electroactive polymer 161c. The portion 161c is arranged in a manner which causes the second portion 161c to deflect in response to a change in electric field provided by the at least two second active area electrodes 164c. A similar arrangement applies to the active areas 162b and 162d.

A substantially rigid frame 167 is fixed to the perimeter of the circular polymer 161 by using an adhesive. A substantially rigid member 168 is attached to a central portion 163 of polymer 161 and allows mechanical output for device 160. Rigid member 168 provides mechanical output for device 160 based on deflection of the central portion 163 relative to the rigid frame 167. The central portion 163 is located at least partially between active area 162a and active area 162c and at least partially between active area 162b and active area 162d. Although central portion 163 is illustrated as a centrally located circle, it should be understood that central portion 163 may be any portion of polymer 161 between the active areas 162a-d. Thus, rigid member 168 may be attached to polymer 161 in any part of polymer 161 between the active areas 162a-d and transfer deflection of that portion as mechanical output of device 160.

The present invention also includes methods for deflecting one or more electroactive polymers having a plurality of active areas. These methods comprise deflection as a result of electrical energy input (actuation) to the polymer and electrical energy output from the polymer (generation). Methods for using a monolithic transducer as an actuator generally comprise providing a change in electric field with two first active area electrodes to deflect a first portion of the monolithic transducer; and providing a change in electric field with two second active area electrodes to deflect a second portion of the monolithic transducer. Other active areas may be used in the monolithic transducer. In one embodiment, active areas on one or more electroactive polymers are sequentially actuated, either individually or cumulatively, to produce a desired deflection of a portion of the polymer. In a specific embodiment, the active areas on a monolithic polymer may be actuated sequentially to move a portion of the polymer along a path.

For example, the active areas 162a-d may be actuated sequentially to move the central portion 163 along a circular path 169. Actuation of the active area 162a moves the central portion 163 down. Actuation of the active area 162b moves the central portion 163 to the left. Actuation of the active area 162c moves the central portion 163 up. Actuation of the active area 162d moves the central portion 163 to the right. When electrical energy is removed from the electrodes 164a, the central portion 163 elastically returns up to its position before actuation of the active area 162a. A similar elastic return occurs for the other active areas 164b-d. To achieve the circular path 169, the active areas 162a-d are actuated sequentially in clockwise order and in a timely manner. More specifically, electrical energy is supplied to the electrodes 164b while the active area 162a contracts. Electrical energy is supplied to the electrodes 164c while the active area 162b contracts.

A similar timing is applied in actuating the other active areas to produce the circular path 169. This sequential clockwise actuation may be repeatedly performed to continuously move the central portion 163 in the circular path 169. Continuous circular output of the central portion 163 may be used to drive a motor. In a specific embodiment, rigid member 168 may be used as a crank in a rotary crank motor. In another specific embodiment, rigid member 168 may be a plate with bearings to allow the plate to move in both planar directions of the plate. The monolithic device 160 then functions as an x-y (two degree-of-freedom) translation table.

The monolithic transducers 150 and 160 illustrated and described herein comprise active areas with similar geometries and symmetrical configurations. It is understood that monolithic polymers of the present invention may comprise one or more active areas each having a non-symmetrical and custom geometry. It is also understood that active areas on a monolithic polymer may be combined in any configuration. These custom geometry active areas and configurations may be used to produce any custom two-dimensional path or output for a portion of a polymer. In another embodiment, the two-dimensional path illustrated above may be achieved with only two active areas without the use of expanding and relaxing pairs as described above. In this case, actuation of one active area and its corresponding elastic return may be used to provide controlled deflection along one linear dimension. Actuation of the other active area and its corresponding elastic return may be used to provide controlled deflection in an orthogonal linear dimension.

Monolithic transducers and devices are not limited to planar deflections. In a specific embodiment, monolithic transducers may be used to deflect and control out-of-plane motion. For example, actuating all four active areas 162a-d at the same time typically will not change the planar position of the centrally attached rigid member 168, but it will reduce the forces from polymer 161 which tend to hold rigid member 168 in the plane of the film. Thus, if rigid member 168 is suitably loaded by an out-of-plane force, such as a spring or gravity, actuating all four active areas 162a-d at once will cause rigid member 168 to move further out of the plane in the direction of the out-of-plane force. By controlling the amount of energizing (e.g. controlling the voltage) on each of the active areas 162a-d, one can thus control the position of a suitably loaded rigid member 168 in three translational degrees-of-freedom.

In another embodiment, monolithic transducers may be used to actuate degrees-of-freedom other than translational degrees-of-freedom. FIG. 1H illustrates a monolithic device 190 having three degrees of freedom in accordance with a specific embodiment of the present invention. The device 190 comprises two frames 191a and 191b positioned adjacent to each other on a single polymer film 192. The two frames 191a and 191b may be separate frames or they may be made as two integral subframes on a single larger frame of the desired shape. Within each of the frames 191a and 191b are a set of four active areas 194a-d and 196a-d, respectively, arranged similar to the monolithic device 160. The result is a figure "8" rigid frame with each circular area of the "8" patterned to form a device having four active areas similar to the monolithic device 160. Rigid members 195a and 195b of the two circular areas of the "8" are connected, for example, by a rigid bar 196. As a result of the coupling between the two circular areas of the "8", the total device 190 controls both the planar translational directions of the rigid bar 196, as well as the rotational direction in the plane for the rigid bar 196. For example, the bottom active areas 194c and 196c may both be actuated to move the rigid bar 196 up. Alternatively, the bottom active area 194c and the top active area 196a may both be actuated to rotate the rigid bar 196 clockwise.

The ability to control the x-y planar positions of two separated points on a rigid body in a plane allows control for the x-y position and angular orientation of the rigid body in the plane (3 degrees-of-freedom). Other embodiments of the present invention can even do without the "8" shaped frame and use electrode patterns on a single polymer to control the position of two points of an object connected to the polymer at two separate points, allowing control of two translational and one rotational degree-of-freedom for the object.

By controlling three spatial positions of 3 separate points on a rigid body, one can control all six degrees-of-freedom of the rigid body in space (three translational and three rotational degrees-of-freedom). Thus, by suitable combinations of electrode patterns one can control all 6 degrees-of-freedom of a rigid body, or even all six degrees-of-freedom of multiple rigid bodies, using a single polymer film. The advantage of this design is that only a single piece of film and frame is needed to control multiple degrees-of-freedom rather than multiple films and frames, thereby simplifying the device, reducing manufacturing cost, reducing assembly steps, and reducing total size.

Methods for using a monolithic transducer as a generator generally comprise mechanically deflecting the electroactive polymer (or a portion thereof), providing a change in electric field with two first active area electrodes, providing a change in electric field with two second active area electrodes, and mechanically deflecting the electroactive polymer (or a portion thereof) a second time. The order of these events may vary for different generator designs. Typically, the first mechanical deflection occurs before changing the electric field using the two first active area electrodes. This change in electric field provided to the two first active area electrodes is less than the electric field needed to further deflect the first portion associated with the two first active area electrodes. The method also comprises a second mechanical deflection of the first portion after the change in electric field has been provided. Typically, the second mechanical deflection increases the electrical field between the at least two first active area electrodes.

Electroactive polymer material provides a spring force during deflection. Typically, polymer material resists deflection during actuation by its contraction (polymer material outside of an active area) or its expansion (polymer material included in an active area). Removal of the actuation voltage and the induced charge causes the reverse effects. The effects of electroactive polymer elasticity are also witnessed when the polymer is used to convert mechanical energy to electrical energy. In general, when actuation voltages and any external loads are removed, electroactive polymers, or portions thereof, elastically return to their resting position. In one embodiment of the present invention, elastic properties of one or more portions of an electroactive polymer are considered when arranging active areas on a monolithic polymer. In a specific embodiment, a monolithic polymer of the present invention is arranged such that deflection of a portion of the polymer in response to a change in electric field is at least partially assisted by elastic energy of another portion. More specifically, elastic return of one portion may be used to assist actuation of another.

Deflection of the active areas 162a-d included in the device 160 may be assisted by elastic energy contributions provided by contractions and expansions of the other active areas 162 and portions of the polymer 161 outside the active areas 162. The active areas 162 are arranged relative to each other such that elastic energy of one active area may assist deflection of another. For example, the active area 162a is arranged relative to the active area 162c such that elastic energy of the active area 162a may assist deflection of the active area 162c. When actuated in a timely manner, contraction of the active area 162a may at least partially assist expansion of the active area 162c, and vice versa. More specifically, deflection of the active area 162a comprises a direction of contraction that is at least partially linearly aligned with a direction of expansion for the active area 162c towards the active area 162a. Advantageously, transferring elastic energy among different portions of a monolithic electroactive polymer may eliminate the need for electroactive forces generated by electrodes for one portion of the polymer to overcome some of the elastic resistance of that portion.

The amount of elastic energy transfer vary. In one embodiment, the total elastic energy contributions provided by different portions of polymer 161 is substantially equal to the elastic energy required to deflect the first active area 162a for a part of the deflection. In another embodiment, the elastic energy contributions provided by different portions of polymer 161 is substantially equal to the elastic energy required to deflect the first active area 162a for an entire deflection corresponding to an actuation of one of the active areas 162.

An active area may include multiple directions of contraction and expansion. Correspondingly, elastic energy generated during actuation of one active area may used to facilitate deflection of more than one other active area. For device 160, the active areas 162 are arranged relative to one another such that elastic return of one active area 162a-d may facilitate deflection of more than one of the other active areas 162a-d in a direction of actuation. More specifically, active areas 162a and 162c are arranged such that contraction of the active area 162a may facilitate expansion of the active area 162c in a direction towards active area 162a. In addition, active areas 162a and 162b are arranged such that contraction of the active area 162a may facilitate expansion of the active area 162b in a direction towards active area 162a.

For device 160, there is a complementary nature of the active areas 162a-d on opposite sides of the rigid member 168. It should be noted that active areas for a monolithic device need not be grouped in complementary pairs as described for the device 160. For example, an odd number of active areas arranged around rigid member 168 may still employ the elastic energy balance features described above. More specifically, three active areas arranged around rigid member 168 at 120 degree intervals may still employ the elastic energy features described above. In this case, the expansion of one active area is paired with the contraction of more than one other active area.

The timing of deflection between active areas may affect elastic energy transfer therebetween. To increase elastic energy transfer for transducer 160, the active areas 161a-d may be actuated at a high enough rate such that elastic return of one active area assists the deflection of more than one active area subsequently actuated. This may be useful for active areas having more than one direction of actuation. For example, to increase elastic energy transfer to the active areas 162b and 161c, actuation of active areas 162b and 161c may begin actuation during elastic return of active area 161a. In this manner, elastic energy generated during actuation of active area 162a is transferred to two active areas 162b and 162c actuated thereafter. A similar timing may be continuously applied as the active areas 162a-d are actuated in turn to produce the circular path 169.

In one embodiment, actuation of a second active area begins when a first active area is at peak deflection. In one embodiment, an active area in an electroactive polymer is actuated in resonant mode. Operating an electroactive polymer at resonance using materials, such as silicone, with low losses (e.g., low viscoelastic losses) allows energy available from the elastic return to stay in the polymer in the form of resonant mode vibration for use in a subsequent actuation.

Each of the electrode pairs 164a-d are arranged such that they provide independent electrical communication with each of the active areas 164a-d. Independence of the electrodes 164a-d allows electrical energy to be separately supplied to (or removed from) the electrodes 164a-d; thus allowing independent control and separate actuation for each of the active areas 164a-d. In another embodiment, two or more electrodes for a monolithic transducer are electrically coupled. In a specific embodiment, electrically coupled electrodes are included in a common electrode. A common electrode is an electrode that is capable of electrically communicating with more than one active area of an electroactive polymer. In many cases, a common electrode allows monolithic transducers to be implemented with less complexity. Alternatively, a common electrode may be used to sequentially actuate multiple active areas according to a propagation of the electrical charge through the common electrode.

Figure 1E:
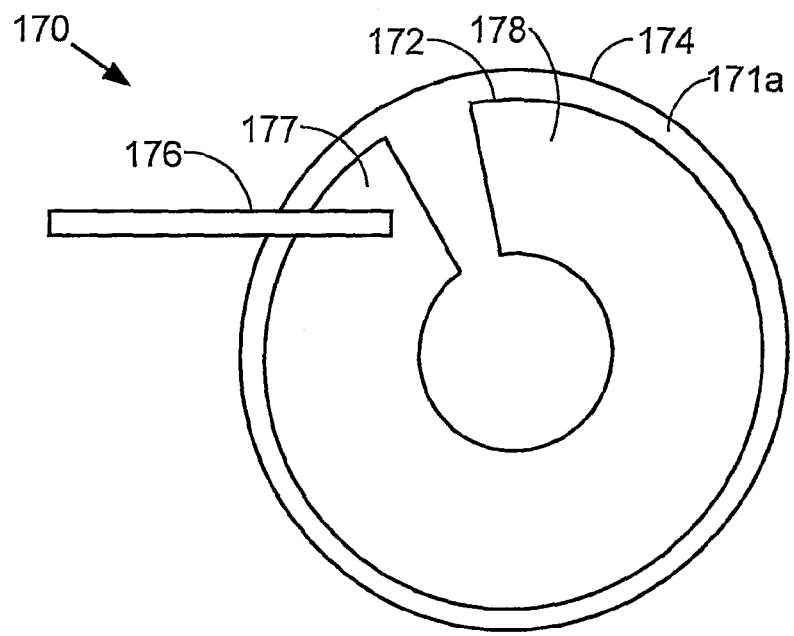
FIGS. 1E and 1F illustrate opposite sides of a monolithic transducer in accordance with a specific embodiment of the present invention.
Figure 1F:
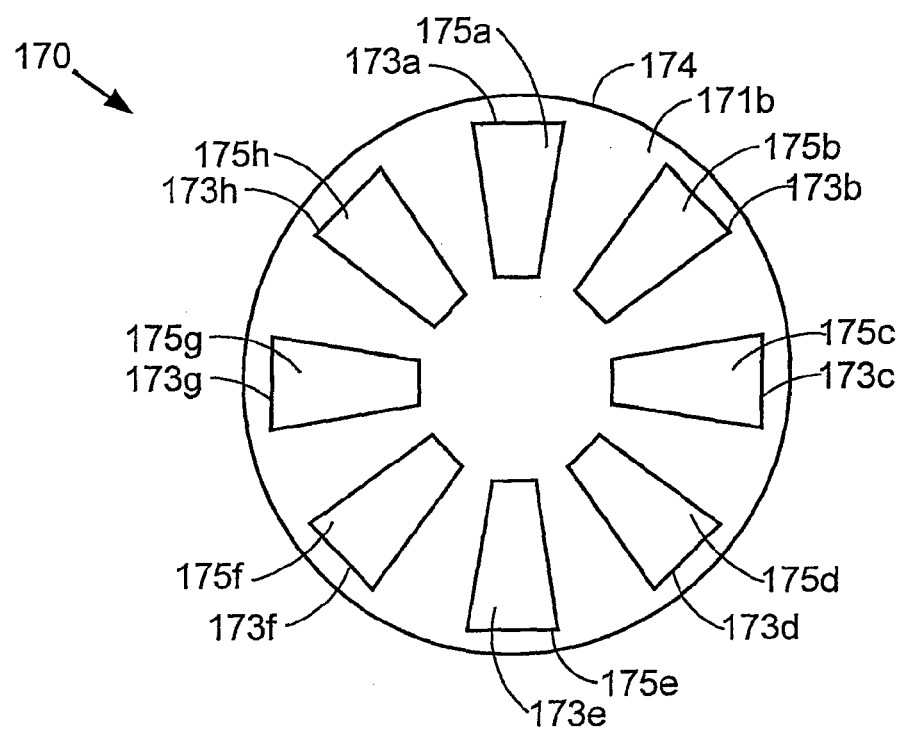

FIGS. 1E and 1F illustrate opposite sides 171a and 171b, respectively, of a monolithic transducer 170 in accordance with one embodiment of the present invention. The monolithic transducer 170 comprises a common electrode 172 on the first side 171a of an electroactive polymer 174 (FIG. 1E). Separate electrodes 173a-h are deposited on the opposite surface 171b (FIG. 1F). The common electrode 172 allows electrical communication with multiple active areas for polymer 174. The common electrode 172 and the separate electrodes 173a-h are provided to produce a voltage difference across multiple portions of polymer 174. Each of the eight active areas 175a-h is individually formed by each of the eight separate electrodes 173a-h, a portion of the common electrode 172 substantially close to the separate electrode, and a portion of the polymer 174 therebetween. More specifically, a first active area 175a is formed by the separate electrode 173a, a portion of the common electrode 172 substantially close to the separate electrode 173a, and a portion of the polymer 174 therebetween. A second active area 175b is formed by separate electrode 173b, a portion of the common electrode 172 substantially close to the separate electrode 173b, and a portion of the polymer 174 therebetween. Electrical communication with each of the active areas 175a-h may be independently achieved using the common electrode 172 and one of the separate electrodes 173a-h. For example, active area 175b may be independently actuated using electrode 173b and the common electrode 172.

Figure 1G:
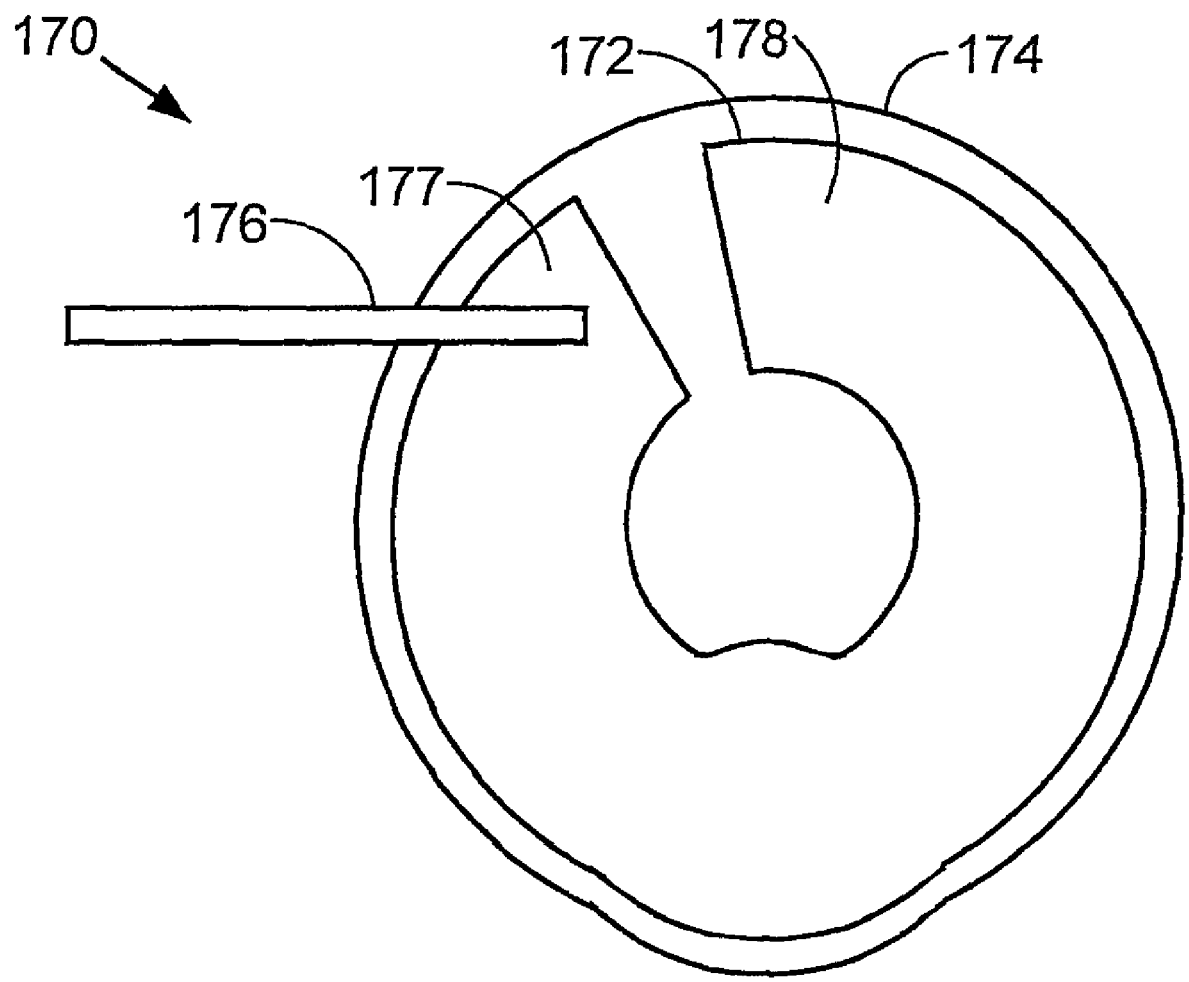
FIG. 1G illustrates deflection of a portion of the monolithic transducer of FIGS. 1E and 1F in accordance with a specific embodiment of the present invention.
Figure 1H:
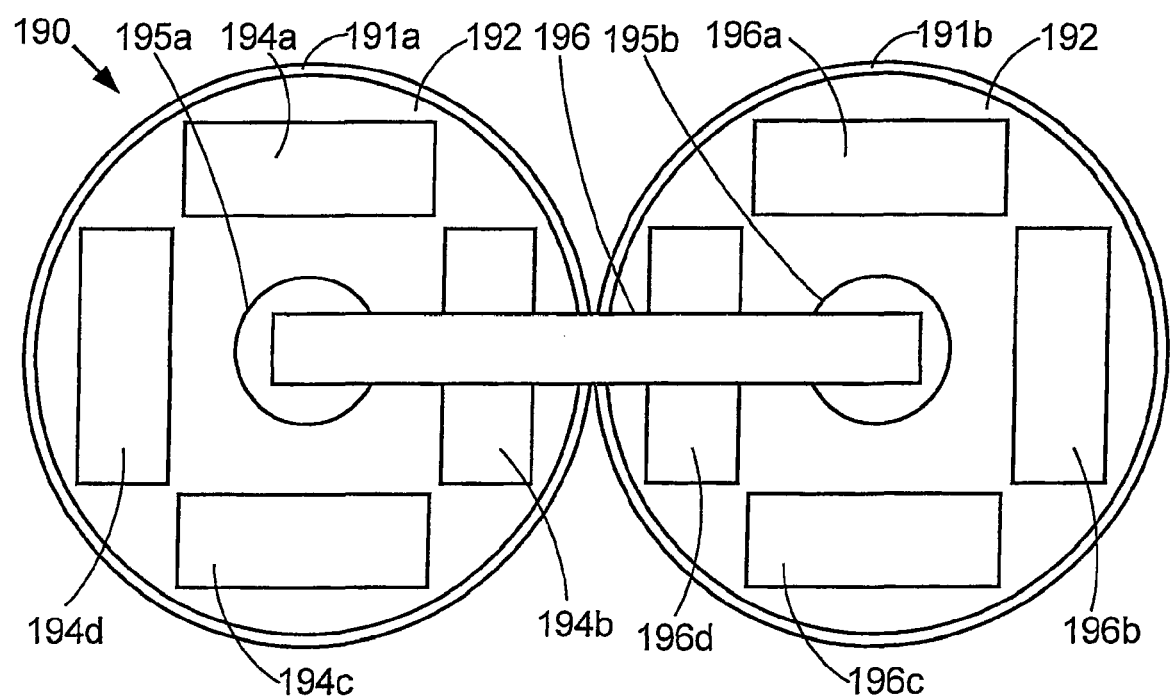
FIG. 1H illustrates a monolithic device providing three degrees of freedom in accordance with a specific embodiment of the present invention.

Each portion of the polymer corresponding to the active areas 175a-h deflects in the plane of the polymer 174 with a change in electric field provided by the common electrode 172 and/or one of the separate electrodes 173a-h. For example, the actuation of active area 175e (FIG. 1F), using electrode 173e and the common electrode 172 causes polymer 171 between the these electrodes to locally expand in the plane, as illustrated in FIG. 1G. The common electrode 172 and separate electrode 173e are both compliant and also deflect with polymer 171. When electric energy is removed from the active area 175e, there is insufficient electrical energy in the active area 175e to maintain deflection and elastic return of polymer 171 returns the active area 175e to its resting state (FIG. 1E).

In one embodiment, the electrical energy for actuating each of the active areas 175a-h is provided using the common electrode 172. In this case, electrical energy is supplied by a lead 176 at the initiating end 177 of the common electrode 172 and flows to the distal end 178. As electrical energy flows through the common electrode 172, each portion of the polymer corresponding to the active areas 175a-h deflects when it has sufficient electrical energy. As charge provided by the lead 176 flows counterclockwise through the common electrode 172, portions of polymer 174 having sufficient electrostatic energy will deflect in turn according to a counterclockwise propagation of the charge. Thus, when charge in the common electrode 172 reaches the bottom portion of the common electrode 172, polymer 174 deflects as illustrated in FIG. 1G. The common electrode 172 is compliant and deflects with the polymer 174.

In another embodiment, a common electrode 172 is deposited on both sides of polymer 174. In this case, a second lead is attached to the second common electrode on the opposite side of the polymer 174. The two leads may then be used to apply a voltage difference between the electrodes. The second common electrode can be considered as a limiting case of an infinite number of active areas connected together on one side of the film.

Portions of polymer 174 deflecting as a result of actuation elastically return to their resting position after the electrical charge has been removed. Removal of electric charge from polymer 174 may be obtained by removing the charge from the common electrode 172. When two common electrodes are used on either side of polymer 174, removal of electric charge from the polymer 174 may achieved by removing the voltage applied between the lead 176 and the second lead on the opposite side.

Electrical energy may be repetitively applied and removed using the common electrode 172. By applying and removing voltage across lead 176 and a lead for the common electrode on the opposing side of the polymer, a wave-like effect is then produced by sequential deflection of portions of the polymer 174 as charge flows counterclockwise through the common electrode 172. This wave-like effect may be repeatedly produced by repeatedly applying and removing voltage across lead 176 and a lead for the opposite common electrode.

For wave-like actuation of two common electrodes on either side of polymer 174 in this manner, or sequential actuation using a common electrode 172 and separate electrodes 173a-h, timing of actuation for each of the active areas 175a-h is modulated by a propagation of charge through the common electrode 172. The propagation delay may be varied either by electrically controlling the voltage on the separate electrodes 173a-h, by connecting the separate active area 173a-h in series with a suitable resistance between each active area to effect a resistance-capacitance time delay, or by designing the resistance of the common electrode 172 to achieve a desired propagation delay. In one embodiment, a highly resistive material is used to increase the time it takes for charge to propagate through the common electrode 172. In another embodiment, the separate electrodes 173a-h are in electrical communication, e.g., using a wire connecting therebetween, and used to modulate a propagation of charge through electrodes 173a-h.

In a specific embodiment, the common electrode has a surface resistivity in the range of about 0.01 M$\square$ to 50 M$\square$ per square. These ranges are given as exemplary numbers, but the actual value chosen depends on the device and the desired propagation delay. An initial estimate of the desired surface resistivity can be obtained by setting the RC time constant (where R is the resistance and C is the polymer capacitance counting all active areas as parallel capacitances) to be equal to the desired time delay for the actuation to propagate around the device. The value of surface resistivity may then be adjusted by experimentation. Decreasing the resistance shortens the time delay, and increasing the resistance increases the time delay. The resistance of the common electrode is controlled during fabrication by using higher resistance electrode materials, or by adjusting the electrode thickness to change its resistance.

The common electrode 172 reduces the complexity of the monolithic transducer 170. This may be advantageous for simplifying and reducing costs of devices with numerous electrodes that may be replaced by a common electrode. Applying the common electrode 172 to both sides of the monolithic transducer 170 may further simplify a design. Although the common electrode 172 is illustrated as electrically communicating with all the active areas on one side of the transducer 170, it is understood that a common electrode in accordance with the present invention may electrically communicate with a subset of the active areas of an electroactive polymer.

4. ACTUATOR AND GENERATOR DEVICES

The deflection of an electroactive polymer can be used in a variety of ways to produce or receive mechanical energy. Generally, monolithic electroactive polymers of the present invention may be implemented in a variety of actuators and generators—including conventional actuators and generators retrofitted with a monolithic polymer and custom actuators and generators specially designed for one or more monolithic polymers. Conventional actuators and generators include extenders, bending beams, stacks, diaphragms, etc. Several exemplary actuators and generators suitable for use with the present invention will now be discussed. Additional actuators suitable for use with various embodiments of the present invention are described in copending U.S. patent application Ser. No. 09/619,848, which was incorporated by reference above.

Figure 2A:
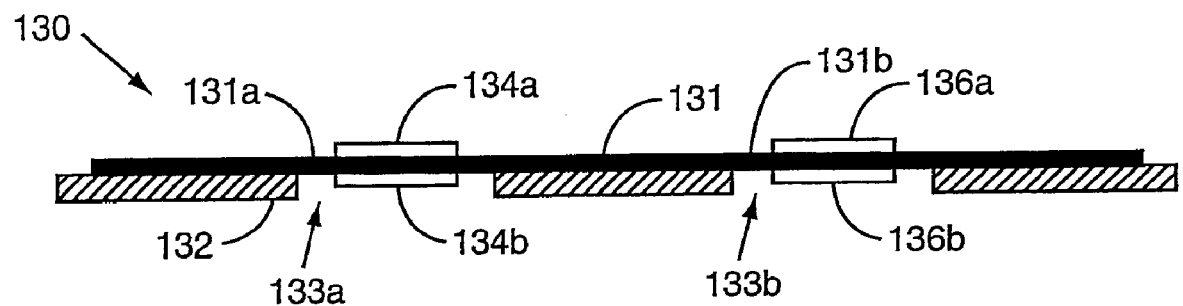
FIGS. 2A and 2B illustrate a device comprising a monolithic transducer for converting between electrical energy and mechanical energy in accordance with another embodiment of the present invention.

FIG. 2A illustrates a cross-sectional side view of a monolithic diaphragm device 130 comprising a monolithic polymer 131 before deflection in accordance with one embodiment of the present invention. The polymer 131 is attached to a frame 132. The frame 132 includes apertures 133a and 133b that allow deflection of polymer portions 131a and 131b perpendicular to the area of the apertures 133a and 133b, respectively. The diaphragm device 130 comprises electrodes 134a and 134b attached on either side of the portion 131a to provide a voltage difference across the portion 131a. Electrodes 136a and 136b are deposited on either side of the portion 131b to provide a voltage difference across the portion 131b. The electrodes 134 and 136 are compliant and change shape with polymer 131 as it deflects. In the voltage-off configuration of FIG. 2A, polymer 131 is stretched and secured to frame 132 with tension to achieve pre-strain.

Figure 2B:
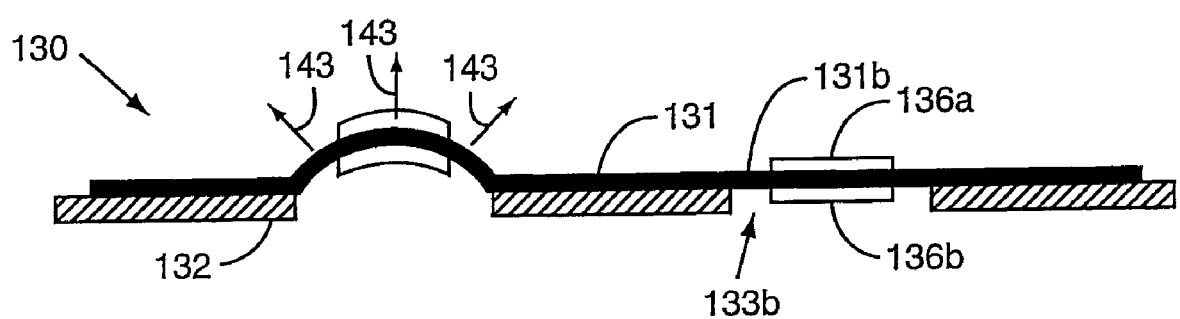

Using electrodes 134 and 136, portions 131a and 131b are capable of independent deflection. For example, upon application of a suitable voltage between electrodes 134a and 134b, portion 131a expands away from the plane of the frame 132, as illustrated in FIG. 2B. Each of the portions 131a and 131b is capable of expansion in both perpendicular directions away from the plane. In one embodiment, one side of polymer 131 comprises a bias pressure that influences the expansion of the polymer film 131 to continually actuate upward in the direction of arrows 143 (FIG. 2B). In another embodiment, a swelling agent such as a small amount of silicone oil is applied to the bottom side to influence the expansion of polymer 131 in the direction of arrows 143. The swelling agent allows the diaphragm to continually actuate in a desired direction without using a bias pressure. The swelling agent causes slight permanent deflection in one direction as determined during fabrication, e.g. by supplying a slight pressure to the bottom side when the swelling agent is applied.

The diaphragm device 130 may be used as a generator. In this case, a pressure, such as a fluid pressure, acts as mechanical input to the diaphragm device 130 on one side to stretch polymer 131 in the vicinity of apertures 133a and 133b. After the stretch, a voltage difference is applied between electrodes 134 while portions 131a is stretched. The resulting change in electric field provided to electrodes 134 is less than the electric field needed to further deflect polymer 131a. Similarly, a voltage difference is applied between electrodes 136 while portion 131b is stretched. Releasing the pressure allows portions 131a and 131b to contract and increase the stored electrical energy on electrodes 134 and 136.

Although the monolithic diaphragm device 130 is illustrated and described with only two apertures that allow deflection of polymer portions perpendicular to the area of the apertures, it is understood the monolithic diaphragm device 130 may include a large number of apertures in any two dimensional array. Generally, an array for a monolithic polymer refers to a plurality of active areas on a single polymer arranged in any manner, number of configuration. For example, the diaphragm device 130 may include an array of 36 active areas arranged in a 6×6 grid. Alternatively, the array on a monolithic polymer may include a combination of custom geometry active areas. These separate active areas may or may not interact mechanically or electrically with each other. In one embodiment, at least two active areas in the array are capable of independent electrical communication and control.

Figure 2C:
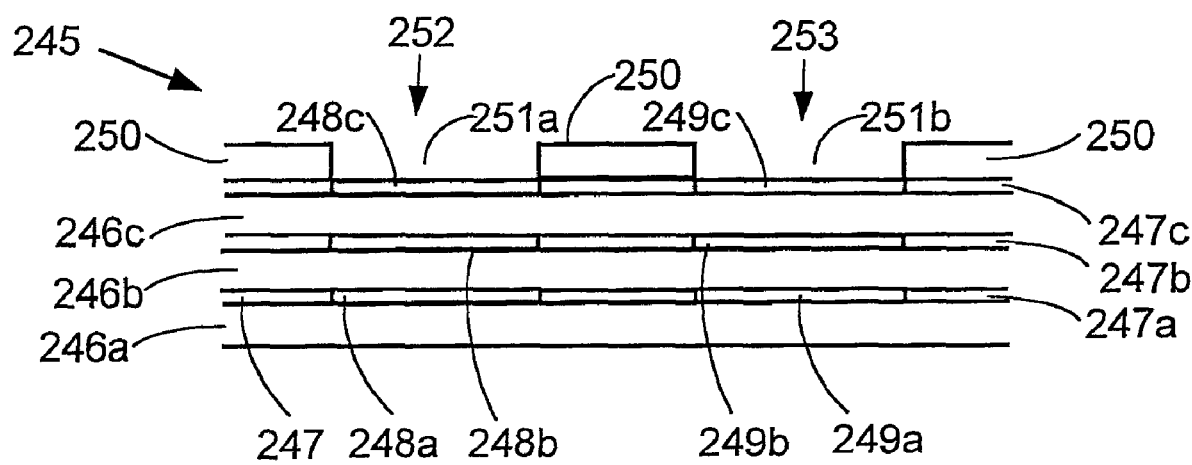
FIG. 2C illustrates a stacked multilayer device suitable for use with the present invention.

In addition, multiple electroactive polymer layers may be used in place of a single polymer to increase the force or pressure output of an actuator. FIG. 2C illustrates a stacked multilayer device 245 suitable for use with the present invention. The stacked multilayer device 245 comprises three polymer layers 246a-c layered upon each other and attached by adhesive layers 247a-c. A rigid plate 250 is attached to the outermost polymer layer 246c and patterned to include a first hole 251a and a second hole 251b that guide deflection for left and right portions 252 and 253 of the polymer layers 246a-c, respectively. Within the adhesive layers 247 are electrodes 248a-c and 249a-c that provide actuation to left and right portions 252 and 253 of the polymer layers 246a-c, respectively. Upon actuation of the polymer layers 246a-c, the holes 251 guide deflection of the polymer layers in a direction substantially perpendicular to holes 251. For example, hole 251a guides deflection of the left portion 252 of polymer layers 246a-c in a direction substantially perpendicular to hole 251a. The left and right portions 252 and 253 of polymer layers 246a-c are capable of independent deflection. By combining the polymer layers 246a-c, the stacked multilayer device 245 provides cumulative force output of the individual polymer layers 246.

Figure 2D:
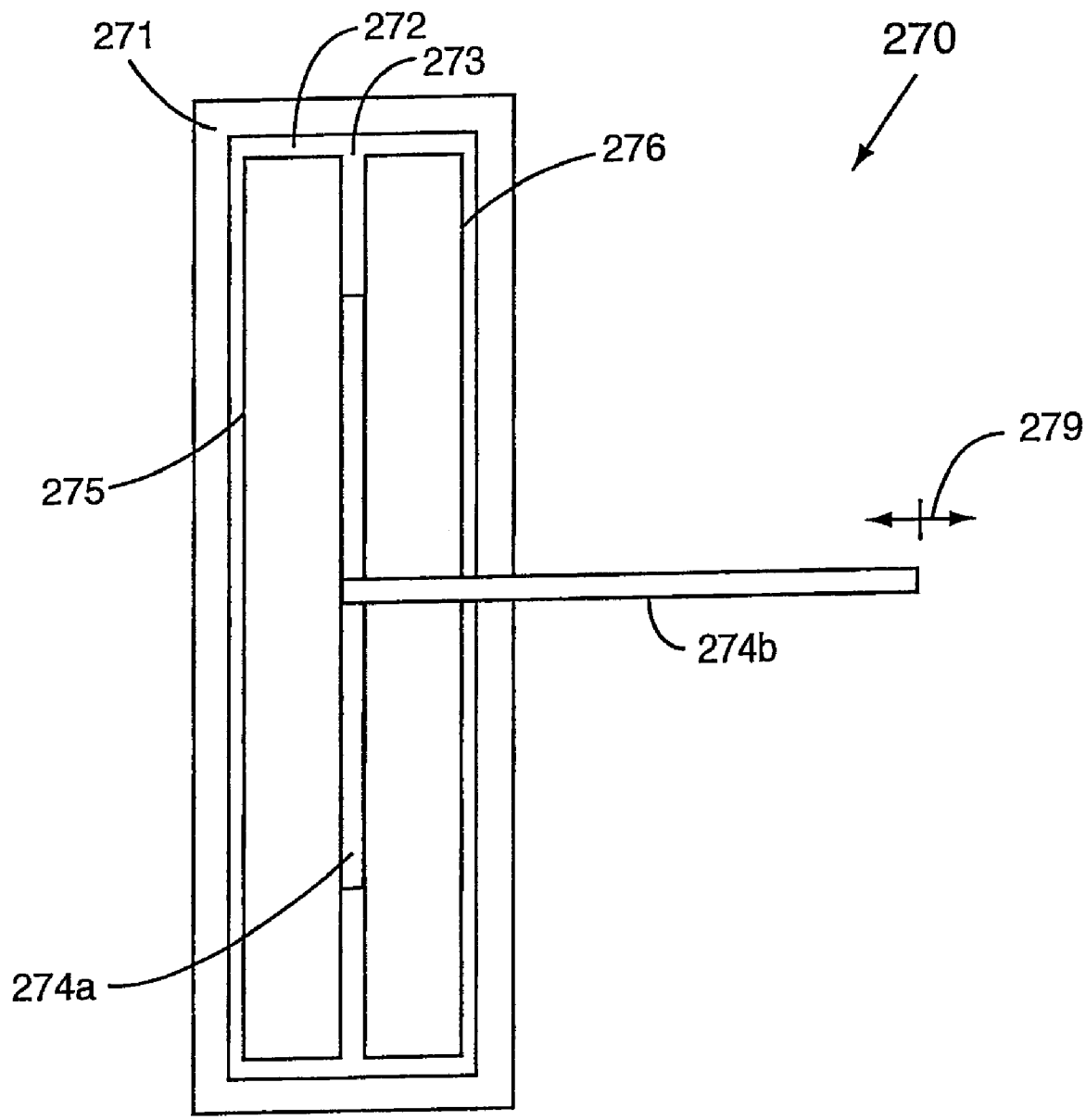
FIG. 2D illustrates a stretched film device in accordance with one embodiment of the present invention.

FIG. 2D illustrates a stretched film device 270 in accordance with another embodiment of the present invention. The stretched film device 270 comprises a rigid frame 271 having a hole 272. The perimeter of a monolithic electroactive polymer 273 is attached in tension to the frame 271 and spans the hole 272. A substantially rigid member 274 includes two segments 274a and 274b. The first segment 274a is attached to the center of the polymer 273. The second segment 274b provides mechanical output corresponding to deflection of the polymer 273.

Compliant electrode pairs 275 and 276 are patterned on both opposing surfaces of the polymer 273 and on the left and right sides of the first segment 274a, respectively. The second segment 274b is capable of motion assisted by deflection of the polymer in response to a change in electric field provided by electrode pairs 275. When the electrode pair 275 is actuated, a portion of the polymer 273 between, and in the vicinity of, the electrode pair 275 expands relative to the rest of the polymer 273 to move the second segment 274b to the right. Conversely, when the electrode pair 276 is actuated, a second portion of the polymer 273 affected by the electrode pair 276 expands relative to the rest of the polymer 273 and pushes the second segment 274b to move to the left. Alternating actuation of the electrodes 275 and 276 provides a total stroke 279 for the second segment 274b.

One variation of the stretched film device 270 includes adding an anisotropic pre-strain to the polymer such that the polymer has high pre-strain (and stiffness) in the direction perpendicular to the rigid bar displacement. This increases the stroke 279. The first segment 274a can be different lengths depending on the size of the polymer 273 and its prestrain. In one embodiment, the first segment 274a is about 75% of the length of the hole 272 along the direction of the central attachment (perpendicular to stroke 279). When acting as a generator, the second segment 274b is capable of motion that causes a change in electric field in the polymer associated with electrode pairs 275.

Monolithic devices can use a wide variety of electrode patterns with rigid member outputs. In a preferred embodiment, a rigid member, such as rigid member 168 in FIG. 1D or rigid member 274 in FIG. 2D, is designed for high force coupling to the polymer. If the rigid member attachment is too small compared to the cross section of the active area perpendicular to the direction of motion, then the compliance of the polymer will prevent the active element from transmitting most of its actuation force. For example, if rigid member 168 in FIG. 1D were only attached at a small point on polymer 161, then when one of the active areas 162a-d is actuated, the force generated could only be transmitted at that small point. With just a point attachment, a significant portion of the polymer deflection would just go around the point when the rigid member 168 is loaded with force.

Thus, in one embodiment for good force coupling to active areas of the polymer, the length of the attachment between the rigid member and the polymer in a direction perpendicular to a degree of freedom of the rigid member is greater than or comparable to the length of the active area or corresponding electrodes perpendicular to the desired motion of each active area. For example, if rigid member 168 was attached rigidly over most of the electrically inactive central portion of polymer in FIG. 1D, then the attachment length perpendicular to the desired motion of each active area 162a-d would be substantially comparable to the length of each active area perpendicular to a desired direction of motion for each active area 162a-d. For irregularly shaped active areas (i.e., not rectangles or squares), the length of the active area perpendicular to a desired motion of each active area may be taken as the maximum length of the active area perpendicular to the desired motion of each active area.

In some cases, however, the rigid element cannot be attached over the full perpendicular length of the active area. For example, in FIG. 2D if rigid member 274 were attached over the full length then it would extend all the way to, or very close, to the rigid frame 271. In this case, the rigid frame might inhibit output motion of the device 270. Thus, in another embodiment for good force coupling to maintain good deflection, the length of the attachment between the rigid member and the polymer in a direction perpendicular to the desired motion of each active area is less than 100% of the length of the active area (or corresponding electrodes) perpendicular to the desired motion of each active area. In another embodiment for good force coupling to maintain good deflection, the length of the attachment between the rigid member and the polymer in a direction perpendicular to the desired motion of each active area is greater than 50% of the length of the active area perpendicular to the desired motion of each active area. In a specific embodiment, the device in FIG. 2D uses a rigid bar 274 whose length and attachment is about 75% of the length of the hole 272. More generally, the attachment of rigid elements to the polymer are greater than 25% of the length of the active areas perpendicular to the desired motion of each active area.

5. APPLICATIONS

The devices and methods of the present invention finds use in a broad range of applications where conversion between electrical and mechanical energy is required. These applications include a wide variety of actuators, motors, generators, sensors, robotics, toys, micro-actuator applications and pumps. Transducers of the present invention may be implemented in both the micro and macro scales—thus increasing the range of application. Provided below are several exemplary applications for some of the transducers and devices described above. The exemplary applications described herein are not intended to limit the scope of the present invention. As one skilled in the art will appreciate, the transducers of the present invention may find use in any application requiring conversion between electrical and mechanical energy.

By repeatedly actuating active areas on a monolithic electroactive polymer, continuous deflection of the polymer may produce reciprocating linear motion or continuous rotary motion. Reciprocating linear motion may be converted to continuous rotary motion using clutches, gears, and the like. Continuous rotary motion generated by an electroactive polymer may be used to drive a motor. Combining different ways to configure one or more monolithic electroactive polymers within a motor, different motor designs, scalability of electroactive polymers to both micro and macro levels, and different polymer orientations (e.g., rolling or stacking individual polymer layers) permits a broad range of motor designs having one or more monolithic electroactive polymers. These motors convert electrical energy into mechanical work and find use in a wide range of applications. As one of skill in the art will appreciate, there are countless applications for motors. Due to the weight savings gained by using electroactive polymers in producing mechanical energy for a motor, a motor comprising an electroactive polymer is well suited for motor applications that require lightweight. For example, the present invention is well suited for applications that require a lightweight motor that can operate at low speeds and yet obtain high performance from the electroactive polymer materials. There are countless applications for a lightweight, low rpm, efficient motor.

The present invention is also suitable for use as artificial muscle. In one example of artificial muscle, two or more layers of electroactive polymer are sandwiched together and attached to two rigid plates at opposite edges of each polymer. Electrodes are sealed into the center between each of the polymer layers. Each of the polymer layers may include one or more active areas. An advantage of the layered construction is that multiple electroactive polymer layers may be stacked in parallel to produce a desired force that would otherwise not obtainable using a single polymer layer. In addition, the stroke of a linear device may be increased by adding similar linear motion devices in series.

In another embodiment, monolithic electroactive polymers suitable for use with the present invention may be rolled or folded into linear transducers and devices that deflect axially while converting between electrical energy and mechanical energy. Since the fabrication of monolithic electroactive polymers is often simpler with fewer numbers of layers, rolled actuators provide an efficient manner of fitting a large number of polymer layers into a compact shape. Rolled or folded transducers and devices typically include two or more layers of polymer. Rolled or folded actuators are applicable wherever linear actuators are used, such as robotic legs and fingers, high force grippers, etc.

Monolithic polymers that are rolled into a tubular or multilayer cylinder actuator may be implemented as a piston that expands axially upon actuation. Such an actuator is analogous to a hydraulic or pneumatic piston, and may be implemented in any device or application that uses these traditional forms of linear deflection. An electroactive polymer comprising multiple active areas may also operate at high speeds for a variety of applications including sound generators and acoustic speakers, inkjet printers, fast MEMS switches etc.

6. CONCLUSION

While this invention has been described in terms of several preferred embodiments, there are alterations, permutations, and equivalents that fall within the scope of this invention which have been omitted for brevity's sake. For example, although the present invention has been described in terms of several specific electrode materials, the present invention is not limited to these materials and in some cases may include air as an electrode. In addition, although the present invention has been described in terms of several preferred polymer materials and geometries, the present invention is not limited to these materials and geometries. It is therefore intended that the scope of the invention should be determined with reference to the appended claims.

What is claimed is:

1. A transducer for converting between electrical energy and mechanical energy, the transducer comprising:
    a first active area having at least two first active area electrodes and a first portion of an electroactive polymer arranged in a manner which causes the first portion to deflect in response to a change in electric field provided by the at least two first active area electrodes and/or arranged in a manner which causes a change in electric field in response to deflection of the first portion; and
    a second active area having at least two second active area electrodes and a second portion of the electroactive polymer arranged in a manner which causes the second portion to deflect in response to a change in electric field provided by the at least two second active area electrodes and/or arranged in a manner which causes a change in electric field in response to deflection of the second portion,
    wherein the electroactive polymer has an elastic modulus below 100 MPa.

2. The transducer of claim 1 wherein the first and second active areas are arranged such that deflection of the first portion includes a direction of elastic contraction that is at least partially linearly aligned with a direction of elastic expansion for the second portion.

3. The transducer of claim 1 wherein the first and second active areas are symmetrically arranged.

4. The transducer of claim 3 wherein the at least two first active area electrodes and the at least two second active area electrodes are arranged radially around a central point.

5. The transducer of claim 1 wherein electrical communication between the at least two first active area electrodes and the first portion is independent from electrical communication between the at least two second active area electrodes and the second portion.

6. The transducer of claim 1 wherein one of the at least two first active area electrodes is electrically coupled to one of the at least two second active area electrodes.

7. The transducer of claim 6 wherein the one of the at least two first active area electrodes electrically coupled to the one of the at least two second active area electrodes is a common electrode.

8. The transducer of claim 1 wherein the electroactive polymer includes an additive.

9. The transducer of claim 8 wherein the additive improves at least one of polymer dielectric breakdown strength, maximum linear strain, dielectric constant, elastic modulus, response time, and actuation voltage.

10. The transducer of claim 1 wherein the electroactive polymer is substantially planar.

11. A method for using an electroactive polymer comprising a first active area and a second active area, the first active area having at least two first active area electrodes and a first portion of the electroactive polymer, the second active area having at least two second active area electrodes and a second portion of the electroactive polymer, the method comprising:
    a) providing a change in electric field to the at least two first active area electrodes; and
    b) providing a change in electric field to the at least two second active area electrodes,
    wherein the electroactive polymer has an elastic modulus below 100 MPa.

12. The method of claim 11 further comprising mechanically deflecting the first portion before providing the change in electric field to the at least two first active area electrodes.

13. The method of claim 12 wherein the change in electric field provided to the at least two first active area electrodes is less than the electric field needed to further deflect the first portion.

14. The method of claim 13 further comprising mechanically deflecting the first portion after the change in electric field has been provided, wherein the mechanical deflection after the change in electric field has been provided increases the electrical field between the at least two first active area electrodes.

15. The method of claim 11 wherein the change in electric field provided to the at least two first active area electrodes deflects the first portion.

16. The method of claim 11 wherein the change in electric field provided to the at least two second active area electrodes deflects the second portion.

17. The method of claim 16 wherein the second portion is deflected such that elastic energy of the first portion assists a deflection of the second portion.

18. The method of claim 17 wherein deflection of the second portion begins when the first portion is at a peak expansion.

19. The method of claim 11 wherein the change in electric field provided to the at least two first active area electrodes terminates before the change in electric field provided to the at least two second active area electrodes begins.

20. The method of claim 11 wherein the electroactive polymer includes an additive.

* * * * *